(12) United States Patent
Eberl et al.

(10) Patent No.: US 12,728,224 B2
(45) Date of Patent: Sep. 8, 2026

(54) PATIENT INTERFACE WITH A HEAT AND MOISTURE EXCHANGER

(71) Applicant: RESMED PTY LTD, Bella Vista (AU)

(72) Inventors: Lorenz Eberl, Sydney (AU); Luke Andrew Stanislas, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 452 days.

(21) Appl. No.: 18/564,042

(22) PCT Filed: May 27, 2022

(86) PCT No.: PCT/AU2022/050514
§ 371 (c)(1),
(2) Date: Nov. 24, 2023

(87) PCT Pub. No.: WO2022/246519
PCT Pub. Date: Dec. 1, 2022

(65) Prior Publication Data

US 2024/0238551 A1 Jul. 18, 2024

(30) Foreign Application Priority Data

May 27, 2021 (AU) ................................ 2021901586

(51) Int. Cl.
*A61M 16/10* (2006.01)
*A61M 16/06* (2006.01)

(52) U.S. Cl.
CPC .... *A61M 16/1045* (2013.01); *A61M 16/0666* (2013.01); *A61M 16/0683* (2013.01)

(58) Field of Classification Search
CPC .......... A61M 16/1045; A61M 16/0666; A61M 16/0683; A61M 16/0816; A61M 16/0875;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

WO WO 98/004310 A1 2/1998
WO WO 98/034665 A1 8/1998
(Continued)

OTHER PUBLICATIONS

Extended European Search Report mailed Feb. 24, 2025 in European Application No. 22809973.5, 8 pages.
(Continued)

*Primary Examiner* — Elliot S Ruddie
(74) *Attorney, Agent, or Firm* — Nixon & Vanderhye P.C.

(57) ABSTRACT

A patient interface is disclosed. The patient interface has a plenum chamber and a seal forming structure arranged to form a seal with a region of the patient's face surrounding an entrance to the patient's airways. The patient interface further comprises a heat and moisture exchanger (HME) located within the plenum chamber. The HME comprises a flexible heat and moisture exchange material and a retaining structure formed from a pliable material provided around an outer perimeter of the heat and moisture exchange material. The retaining structure comprises at least one snap fit feature configured to engage, in use, at least one complementary snap fit feature provided to an interior of the plenum chamber; and/or the retaining structure is an interference fit with an interior surface of the plenum chamber. Also disclosed is an HME comprising a flexible heat and moisture exchange material and a retaining structure formed from a thermoplastic.

15 Claims, 34 Drawing Sheets

(58) Field of Classification Search
CPC .......... A61M 16/0066; A61M 16/1005; A61M 16/107; A61M 16/125; A61M 16/16; A61M 16/0003; A61M 16/06; A61M 16/0465; A61M 2016/0027; A61M 2016/0039; A61M 2202/0225; A61M 2205/02; A61M 2205/0216; A61M 2205/3633
USPC ...................................................... 128/201.13
See application file for complete search history.

(56) References Cited

U.S. PATENT DOCUMENTS

| | | | |
|---|---|---|---|
| 5,687,715 A | 11/1997 | Landis | |
| 6,532,959 B1 | 3/2003 | Berthon-Jones | |
| 6,581,594 B1 | 6/2003 | Drew et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 9,155,857 B2 | 10/2015 | Lalonde | |
| 10,695,521 B2 | 6/2020 | Harrington | |
| 10,792,450 B2 | 10/2020 | Holley et al. | |
| 2009/0044808 A1 | 2/2009 | Guney Memduh et al. | |
| 2009/0050156 A1 | 2/2009 | Ng et al. | |
| 2010/0000534 A1 | 1/2010 | Kooij et al. | |
| 2014/0276177 A1 | 9/2014 | Brambilla et al. | |
| 2016/0175552 A1* | 6/2016 | Harrington | A61M 16/06 128/201.13 |
| 2018/0133426 A1 | 5/2018 | Hallett et al. | |

FOREIGN PATENT DOCUMENTS

| | | | |
|---|---|---|---|
| WO | WO 00/78381 A1 | 12/2000 | |
| WO | WO 2004/073778 A1 | 9/2004 | |
| WO | WO 2005/063328 A1 | 7/2005 | |
| WO | WO 2006/074513 A1 | 7/2006 | |
| WO | WO 2006/130903 A1 | 12/2006 | |
| WO | WO 2009/052560 A1 | 4/2009 | |
| WO | WO 2010/135785 A1 | 12/2010 | |
| WO | WO 2012/171072 A1 | 12/2012 | |
| WO | WO 2013/020167 A1 | 2/2013 | |
| WO | WO 2015/161345 A1 | 10/2015 | |
| WO | WO 2016/082001 A1 | 6/2016 | |
| WO | WO 2017/011864 A1 | 1/2017 | |
| WO | WO 2018/053589 A1 | 3/2018 | |
| WO | WO 2020/188495 A1 | 9/2020 | |
| WO | WO 2020/191463 A1 | 10/2020 | |
| WO | WO 2020/208603 A1 | 10/2020 | |
| WO | WO 2020/234778 A1 | 11/2020 | |
| WO | WO-2020240495 A1 * | 12/2020 | A61M 16/0816 |
| WO | WO 2021/046608 A1 | 3/2021 | |
| WO | WO 2022/073075 A1 | 4/2022 | |

OTHER PUBLICATIONS

"Respiratory Physiology", by John B. West, Lippincott Williams & Wilkins, 9th edition published 2012 (8 pages).

International Preliminary Report on Patentability dated Apr. 12, 2023 issued in International Application No. PCT/AU2022/050514 (29 pages).

International Preliminary Report on Patentability dated Aug. 24, 2022 issued in International Application No. PCT/AU2022/050514 (10 pages).

Written Opinion of the International Searching Authority dated Aug. 24, 2022 issued in International Application No. PCT/AU2022/050514 (12 pages).

Office Action mailed Jan. 23, 2026 in European Application No. 22 809 973.5, 8 pages.

* cited by examiner

Relatively Large
Positive Curvature

Relatively Small
Positive Curvature

Zero Curvature

Relatively Small
Negative Curvature

Relatively Large
Negative Curvature

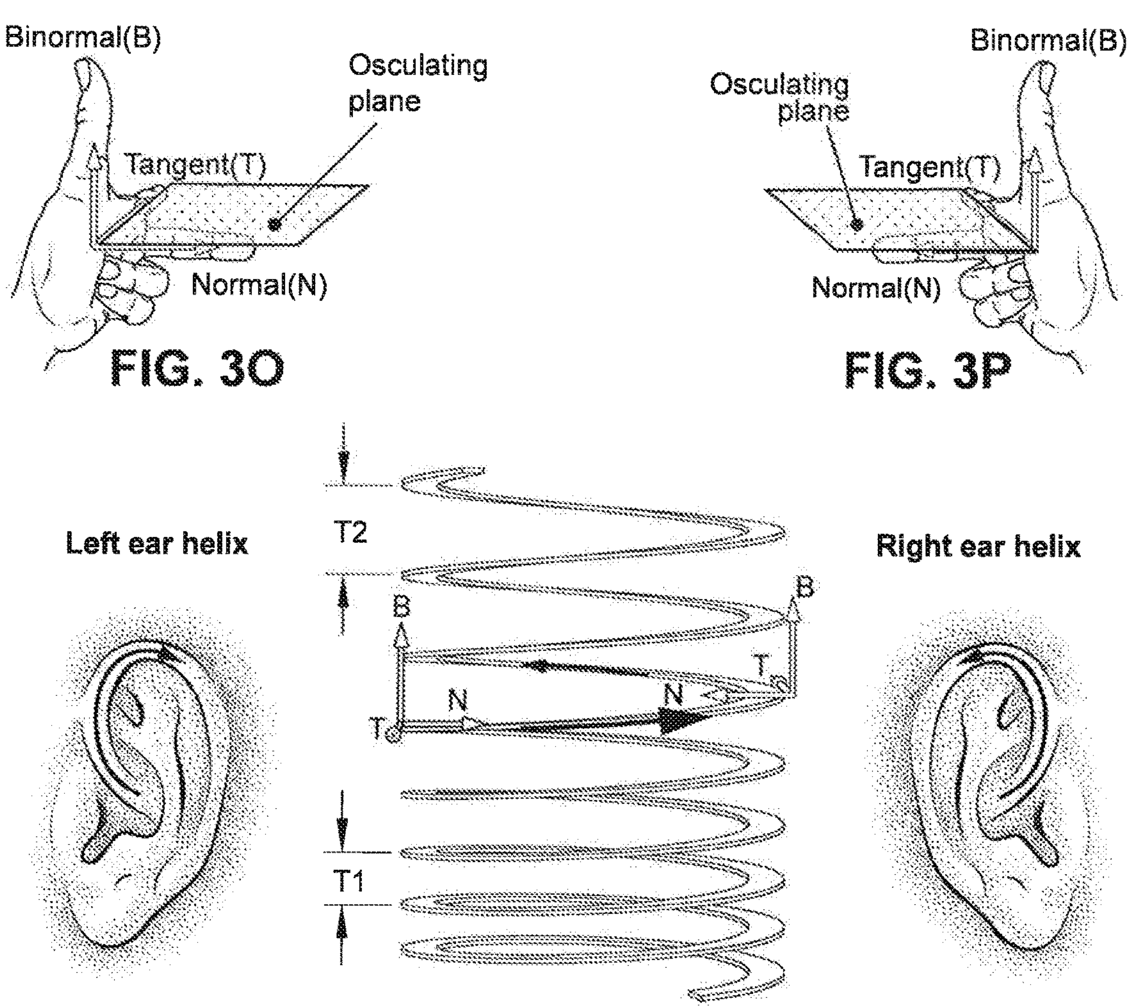
FIG. 3O
FIG. 3P
FIG. 3Q
FIG. 3R
FIG. 3S
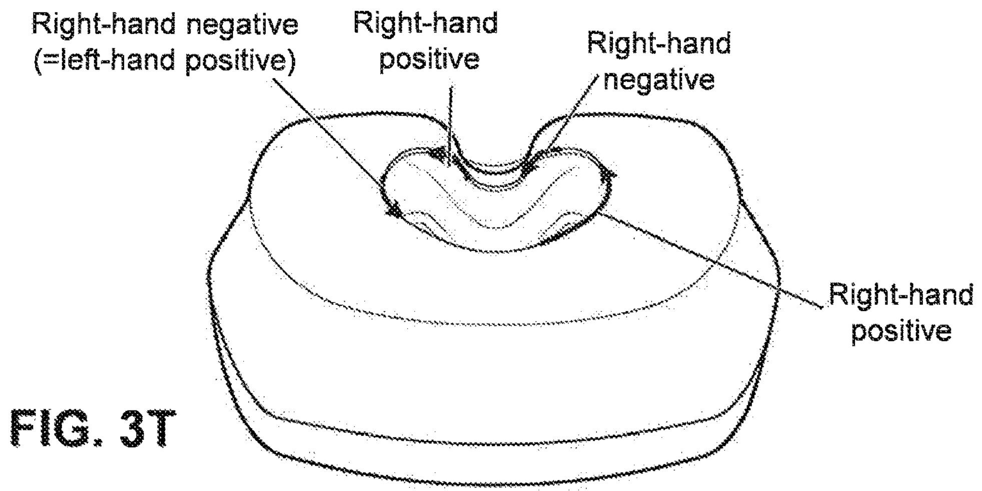
FIG. 3T

PATIENT INTERFACE WITH A HEAT AND MOISTURE EXCHANGER

CROSS-REFERENCE TO RELATED APPLICATIONS

This application is the U.S. national phase of International Application No. PCT/AU2022/050514 filed May 27, 2022 which designated the U.S. and claims priority to AU 2021901586 filed May 27, 2021, the entire contents of each of which are hereby incorporated by reference.

1 BACKGROUND OF THE TECHNOLOGY

1.1 Field of the Technology

The present technology relates to one or more of the screening, diagnosis, monitoring, treatment, prevention and amelioration of respiratory-related disorders. The present technology also relates to medical devices or apparatus, and their use.

1.2 Description of the Related Art

1.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See “Respiratory Physiology”, by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient’s respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient’s needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

1.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube or endotracheal tube. In some forms, the comfort and effectiveness of these therapies may be improved.

1.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that may be held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired CO2 from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

1.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

1.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

1.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

1.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

1.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore, medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

1.2.3.5 Heat and Moisture Exchanger (HME)

Heat and moisture exchangers are generally made up of foam, paper, or an alternative substance capable of acting as a condensation and absorption surface. The material may carry hygroscopic salts to improve the water-retaining capacity. Suitable salts include calcium chloride.

HMEs may be utilized in RPT therapy, such as in PAP therapy, to partially recover heat and moisture present in exhaled gas from a patient's airways. This heat and moisture can be retained and recycled to the patient in a passive manner as a flow of breathable gas passes through the HME prior to inspiration. Thus, the use of HME's can provide at least some of the needed moisture and humidity (generally recognized as >10 mg/l) to most patients during PAP therapy to minimize any detrimental effects associated with PAP therapy with non-humidified ambient air whilst avoiding the need for a heated humidifier system, or at least reducing the load on such a humidifier system if one is present. The use of a HME may also lower the possibility of occlusion caused by condensation in air delivery tubes.

The use of a HME in PAP therapy can avoid or reduce the need for additional power required with heated humidifiers and may reduce the need for extra associated components. This may reduce manufacturing costs and may also reduce the overall size of the CPAP therapy unit.

A problem common with the use of HMEs in CPAP therapy relates to the ability of the HME to provide sufficient heat and moisture while also minimizing flow impedance and maintaining comfortable and safe levels of CO2 washout. Flow impedance may affect patient breathing effort (work of breathing) and may also impact event (apnoea, hypopnoea, snore) detection algorithms, so in many cases it is sought to be minimized. Furthermore, consideration should also be given to minimising heat and moisture loss from venting.

Some current configurations of HME's in RPT therapy have shown negligible patient humidification, have issues with flow impedance, and/or do not allow sufficient CO2 washout. For example, placing the HME unit within the elbow, around the exhaust vent or on the flow generator side of the therapy system has shown issues with impedance and/or CO2 washout with negligible patient humidification (hygroscopic) benefit. One problem with such a configuration is the relatively high proportion of air flow from the RPT which flows through the HME and is then vented to atmosphere without being inspired by the patient. This flow may tend to remove moisture from the HME, and from the patient interface as a whole.

Because the HME creates an impedance to flow from the patient's airways to the vent, patient interfaces which use HMEs may suffer from reduced CO2 washout. This effect may be exacerbated if there is a large volume between the patient's airways and the HME.

Moreover, many current designs of HMEs do not allow for sufficient moisture exchange during patient exhalation to provide sufficient humidification levels to the patient. Thus, there is a need to provide superior configurations and designs for HME use in RPT therapy, such as PAP therapy, to achieve desired patient humidification whilst having acceptable impedance and CO2 washout. It is also desirable that an HME for use with a flexible patient interface does not adversely affect the ability of the patient interface to deform in desirable ways.

1.2.3.6 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

1.2.3.7 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH2O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) (one specimen only, measured using test method specified in ISO 3744 in CPAP mode at 10 cmH2O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

1.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular, it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

2 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a patient interface comprising:

- a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient,
- a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

a positioning and stabilising structure to provide a force to hold the seal-forming structure in a therapeutically effective position on the patient's head; and a vent structure to allow a continuous flow of gases exhaled by the patient from an interior of the plenum chamber to ambient, said vent structure being sized and shaped to maintain the therapeutic pressure in the plenum chamber in use;

wherein the patient interface is configured to allow the patient to breathe from ambient through their mouth in the absence of a flow of pressurised air through the plenum chamber inlet port, or the patient interface is configured to leave the patient's mouth uncovered; and wherein the patient interface comprises a heat and moisture exchanger (HME) located within the plenum chamber between the inlet port and the seal forming structure, the HME comprising a flexible heat and moisture exchange material and a retaining structure formed from a pliable material provided around an outer perimeter of the flexible heat and moisture exchange material, wherein the retaining structure comprises at least one snap fit feature configured to engage, in use, at least one complementary snap fit feature provided to an interior of the plenum chamber and/or the retaining structure is an interference fit with an interior surface of the plenum chamber.

In examples:

a) the retaining structure is formed from a flexible thermoplastic; b) the retaining structure is formed by overmoulding; c) the plenum chamber is formed, at least in part, from a flexible material; d) the heat and moisture exchange material has a patient facing side and a non patient facing side; e) the patient facing side of the heat and moisture exchange material is concave; f) the retaining structure comprises a shaping member which extends across the patient facing side of the heat and moisture exchange material, wherein the shaping member is configured to impart a concave shape to the patient facing side of the heat and moisture exchange material; g) the patient interface is configured to allow air to flow from the inlet port to the vent structure without passing through the HME; h) the snap fit feature of the retaining structure comprises a channel which extends at least partially around the outer perimeter of the retaining structure; i) the channel extends around the entire outer perimeter of the retaining structure; j) the plenum chamber is defined in part by a retaining structure, wherein the complementary snap fit feature is provided to the retaining structure; k) the complementary snap fit feature comprises a rib; l) the HME is configured to provide at least 10 mg/L humidification; and/or m) the heat and moisture exchange material comprises a foam or a non-woven material.

Another aspect of one form of the present technology comprises a patient interface comprising:

a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

a positioning and stabilising structure to provide a force to hold the seal-forming structure in a therapeutically effective position on the patient's head; and a vent structure to allow a continuous flow of gases exhaled by the patient from an interior of the plenum chamber to ambient, said vent structure being sized and shaped to maintain the therapeutic pressure in the plenum chamber in use;

the patient interface is configured to allow the patient to breath from ambient through their mouth in the absence of a flow of pressurised air through the plenum chamber inlet port, or the patient interface is configured to leave the patient's mouth uncovered; and wherein patient interface comprises a heat and moisture exchanger (HME) connected to the seal forming structure.

In examples;

a) the HME is connected to an exterior surface of the seal forming structure; b) the HME is connected to an interior surface of the patient interface; c) the HME comprises foam or a non-woven material and the seal forming structure comprises an engagement formation which engages the foam or non-woven material; d) the engagement formation comprises a channel; e) an outer perimeter of the HME comprises foam; f) the HME is compressed and buckled by the engagement formation; g) the patient interface is configured to allow replacement of the HME; h) the HME is configured to contact the patient when the patient interface is in use; and/or i) the patient interface comprises a first hole for delivery of air to the patient's mouth and a second hole for delivery of air to an entrance to the patient's nares, wherein the patient interface comprises a first HME adjacent the first hole and a second HME adjacent the second hole.

Another form of the present technology comprises a heat and moisture exchanger (HME) for mounting to an interior of a plenum chamber of a patient interface, the HME comprising a flexible heat and moisture exchange material and a retaining structure formed from a thermoplastic provided around an outer perimeter of the flexible heat and moisture exchange material, wherein the retaining structure comprises at least one snap fit feature configured to engage, in use, at least one complementary snap fit feature within the plenum chamber of the patient interface, wherein the retaining structure is formed by overmoulding.

Another form of the technology comprises a patient interface system comprising a plenum chamber pressurisable to a therapeutic pressure of at least 6 cmH2O above ambient air pressure, the plenum chamber having an opening on an anterior side thereof;

a cushion module comprising a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; and a plurality of frames, each frame configured to selectably engage the cushion module, wherein a first of the frames is configured for connection to at least one first tube which is configured to deliver pressurised air to the patient's airways and to function as part of headgear to position and stabilise the seal-forming portion of the patient interface, and a second of the frames is configured for connection to a second tube which is configured to deliver pressurised air to the patient's airways and which does not function as part of the headgear to position and stabilise the seal-forming portion of the patient interface.

In examples, the system further comprises a heat and moisture exchanger (HME) locatable within the plenum chamber, the HME comprising a flexible heat and moisture exchange material and a retaining structure formed from a pliable material provided around an outer perimeter of the heat and moisture exchange material, wherein the retaining structure comprises at least one snap fit feature configured to engage, in use, at least one complementary snap fit feature provided to an interior of the cushion module and/or the retaining structure is an interference fit with the interior of the cushion module.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.2 Respiratory System and Facial Anatomy

Figure 1A:
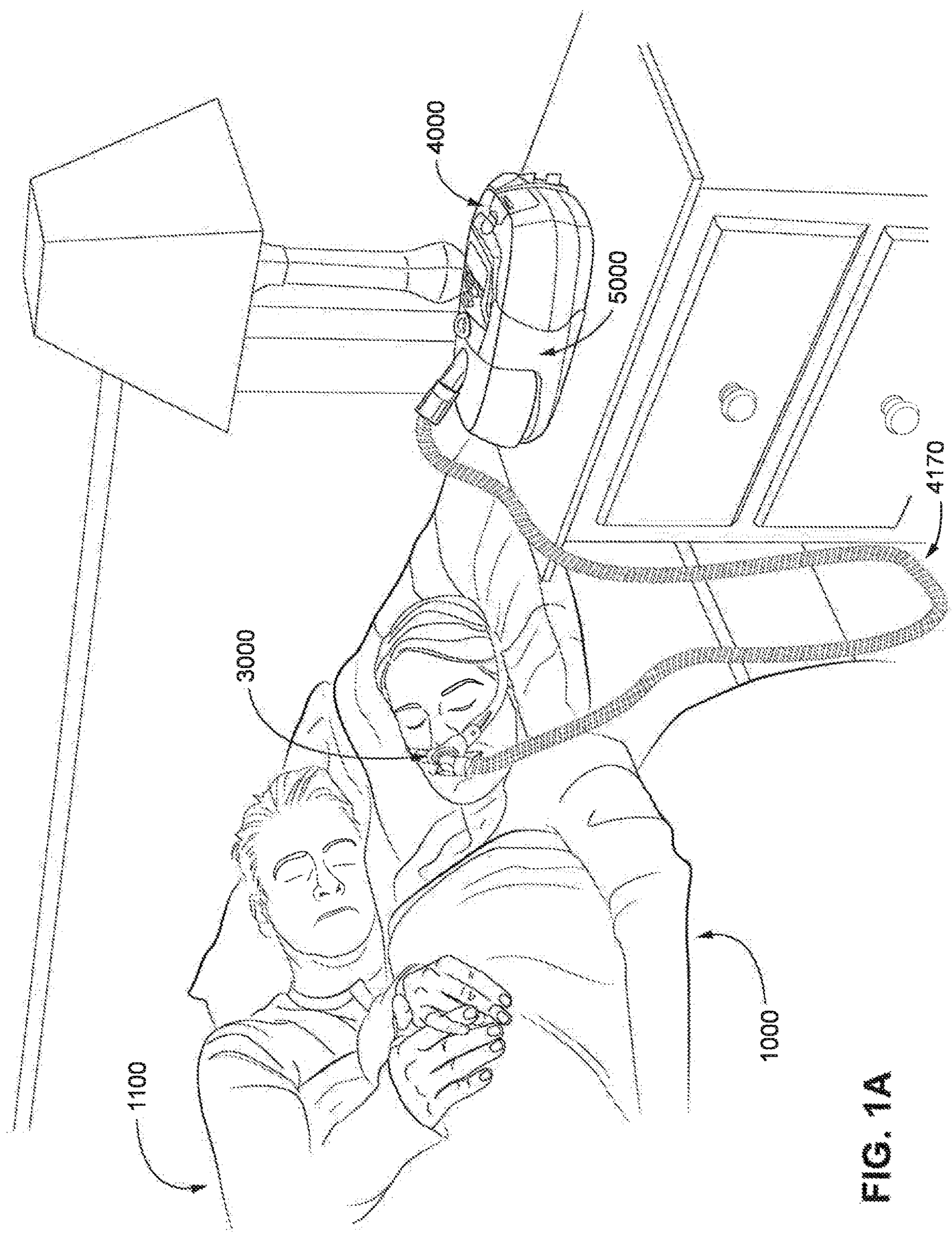
Figure 1B:
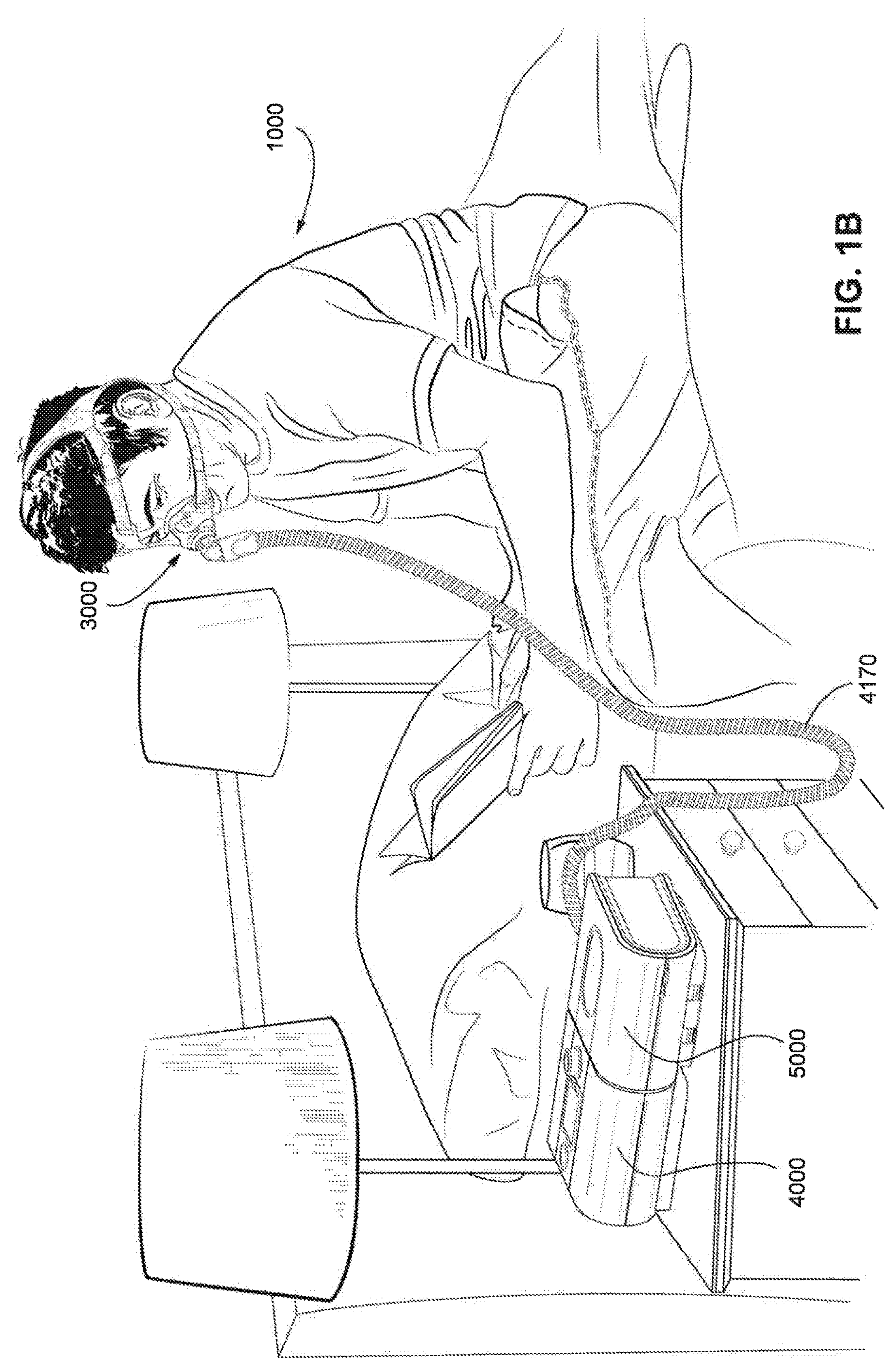
Figure 1C:
Figure 2A:
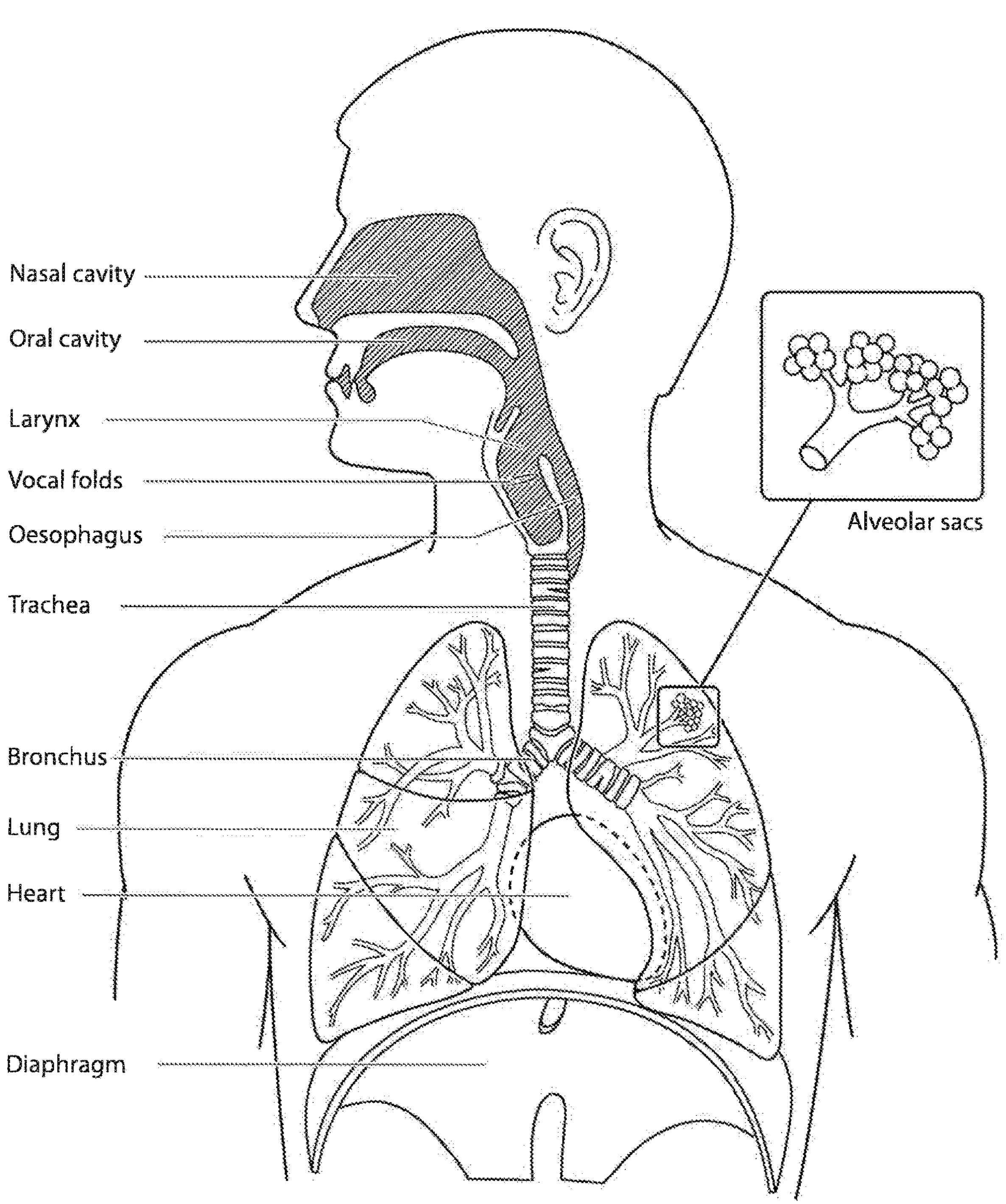
FIG. 2A shows an overview of a human respiratory system including the nasal and oral cavities, the larynx, vocal folds, oesophagus, trachea, bronchus, lung, alveolar sacs, heart and diaphragm.
Figure 2B:
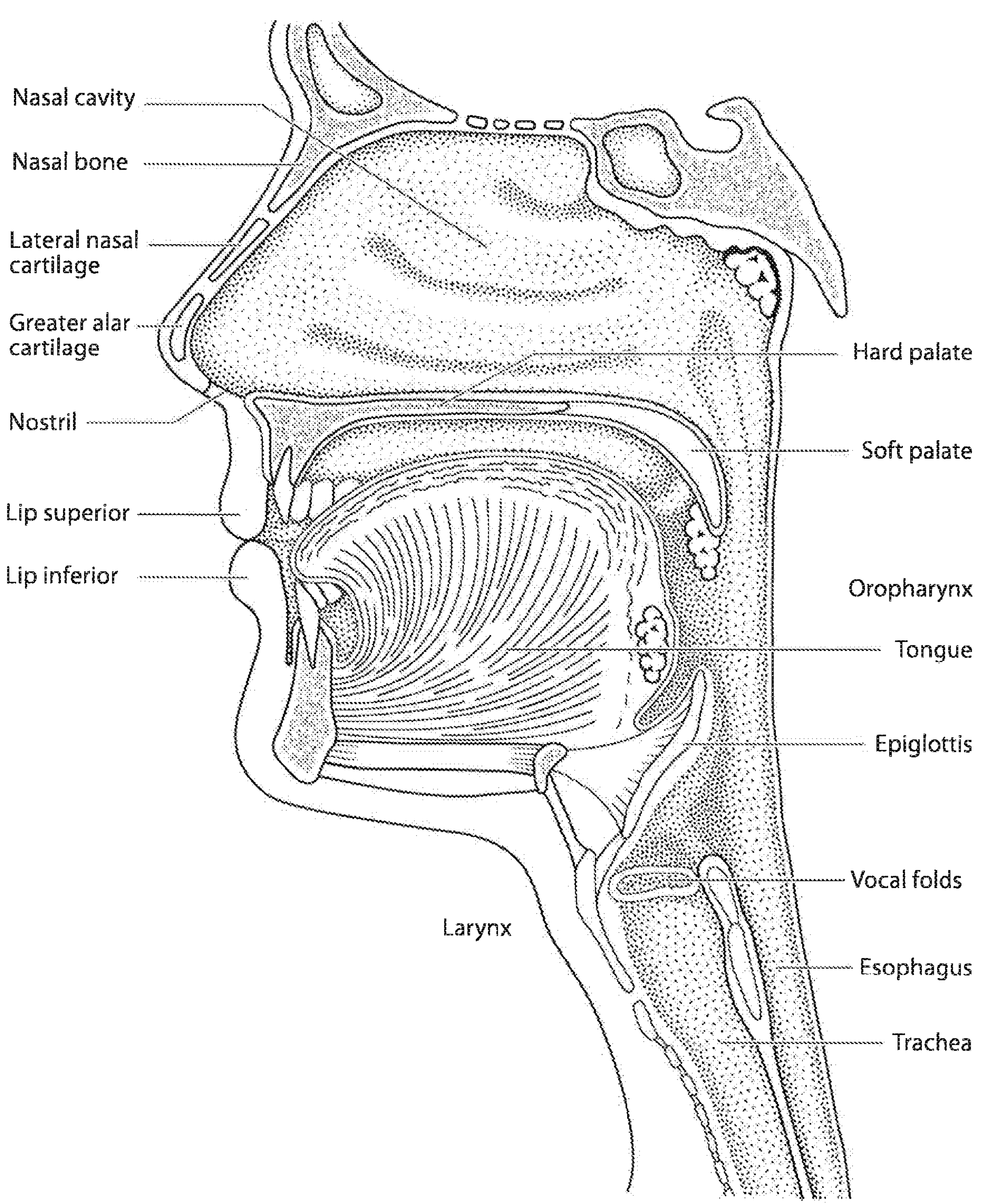
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
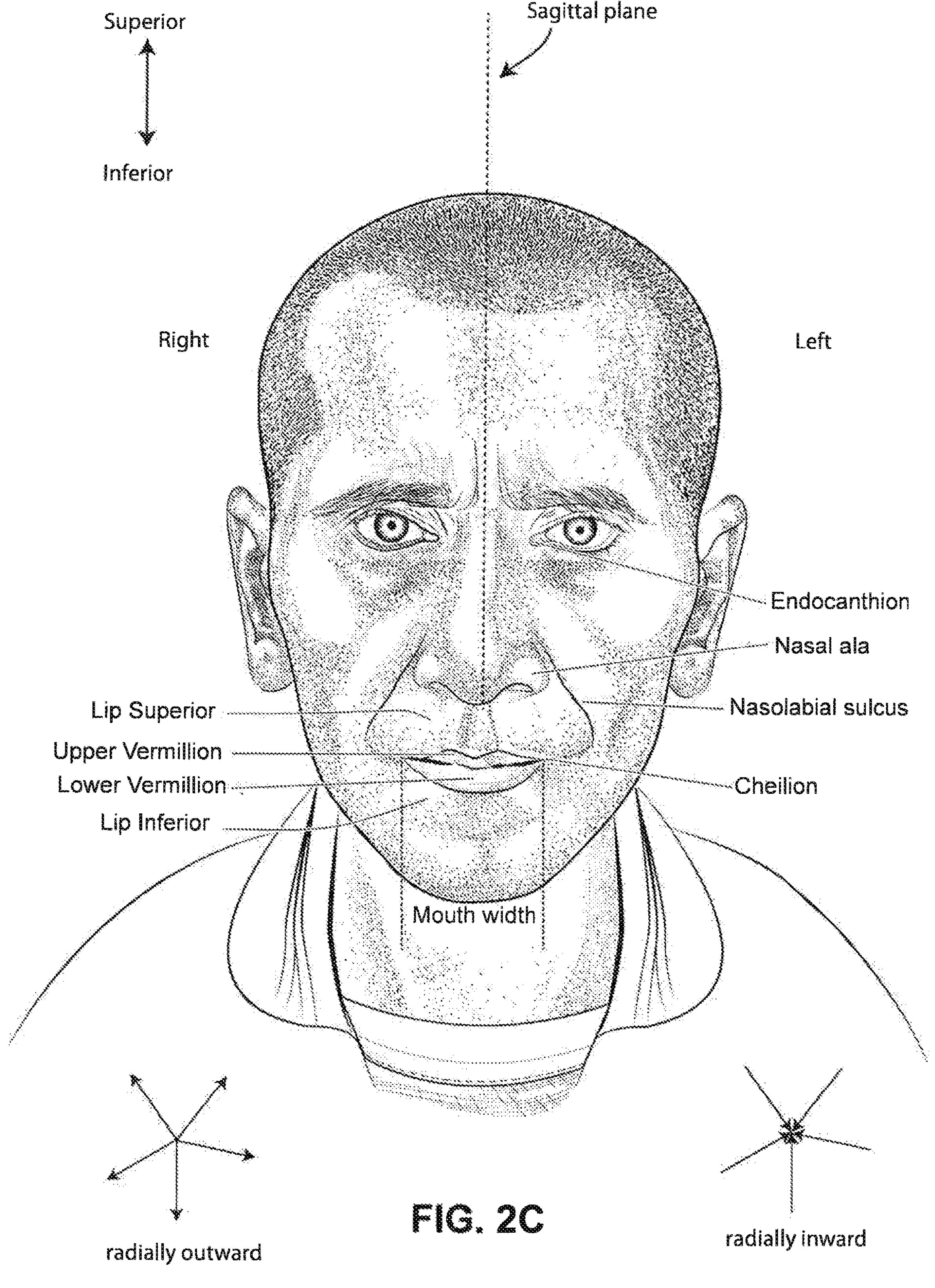
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
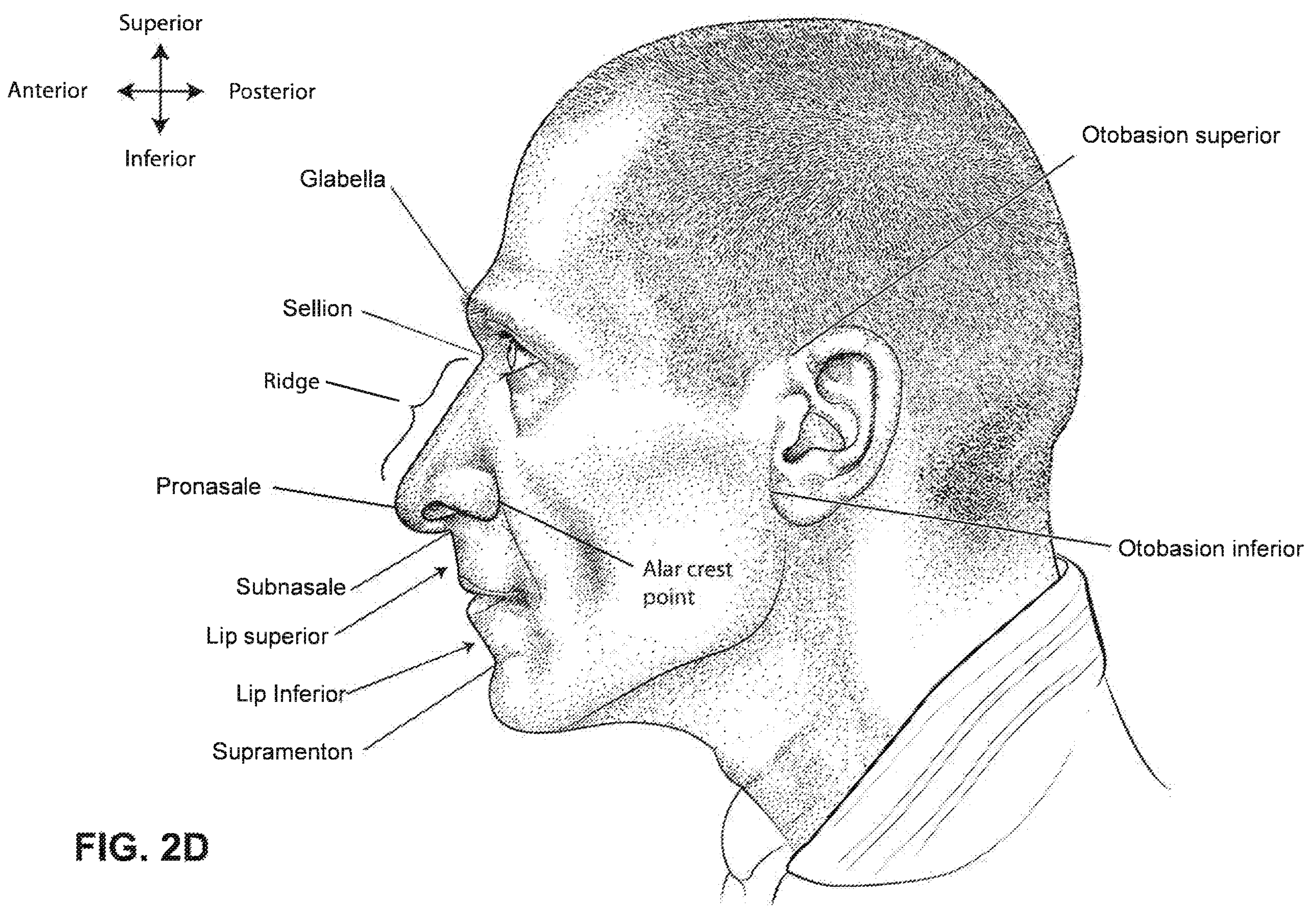
FIG. 2D is a side view of a head with several features of surface anatomy identified including *glabella*, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
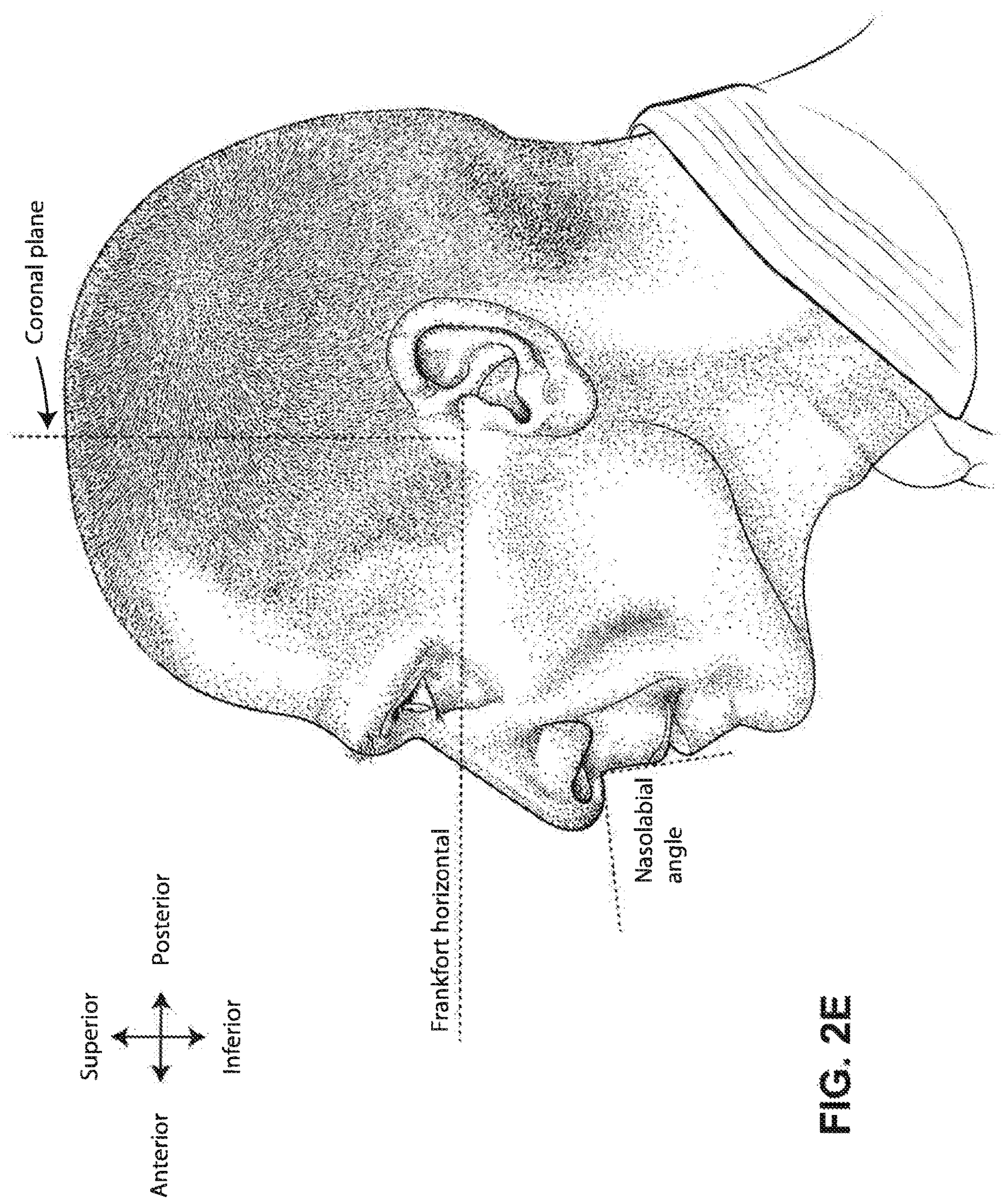

FIG. 2E is a further side view of a head. The approximate locations of the Frankfort horizontal and nasolabial angle are indicated. The coronal plane is also indicated.

Figure 2F:
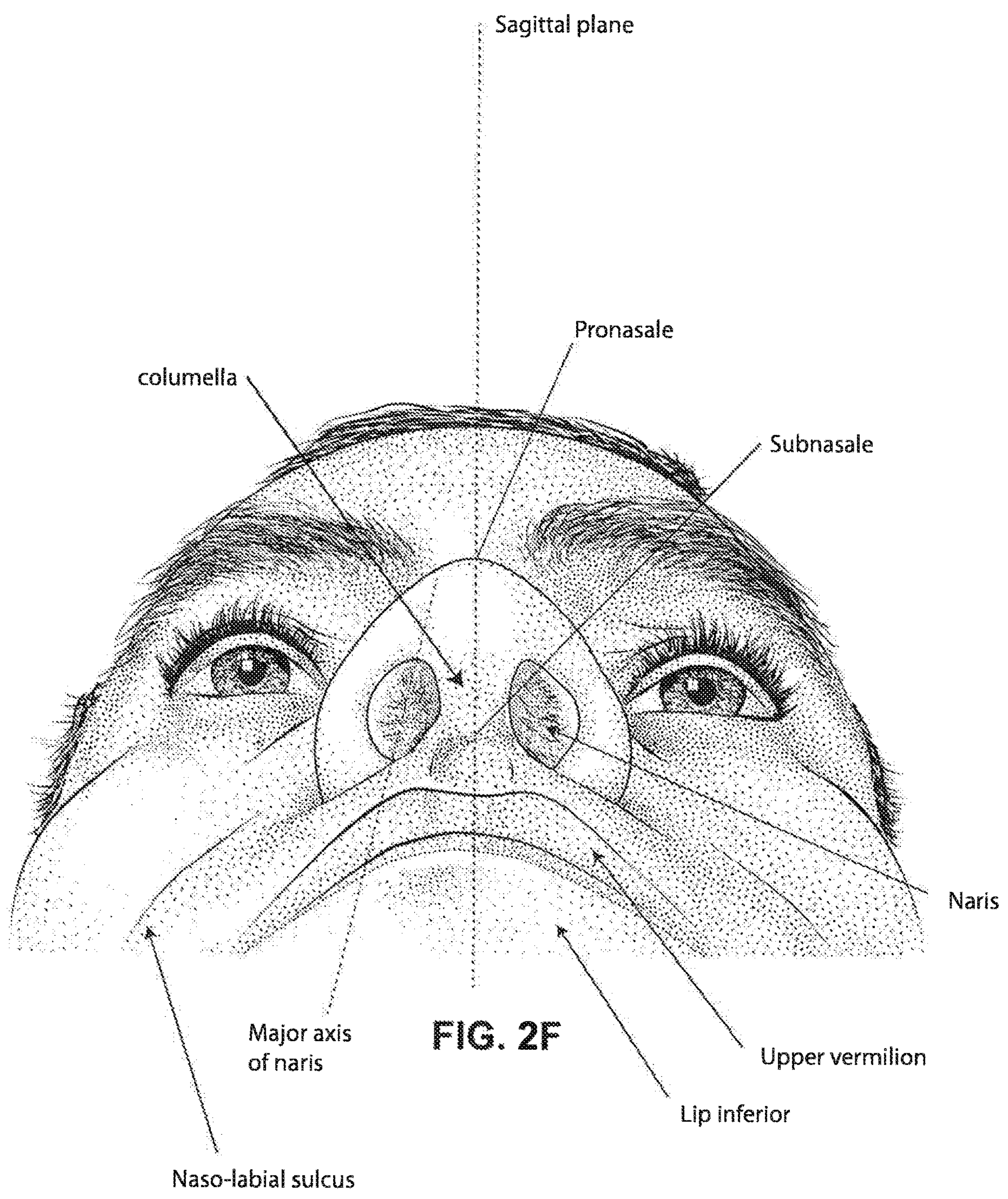

FIG. 2F shows a base view of a nose with several features identified including naso-labial sulcus, lip inferior, upper Vermilion, naris, subnasale, columella, pronasale, the major axis of a naris and the midsagittal plane.

Figures 2G, 2H, 2I:
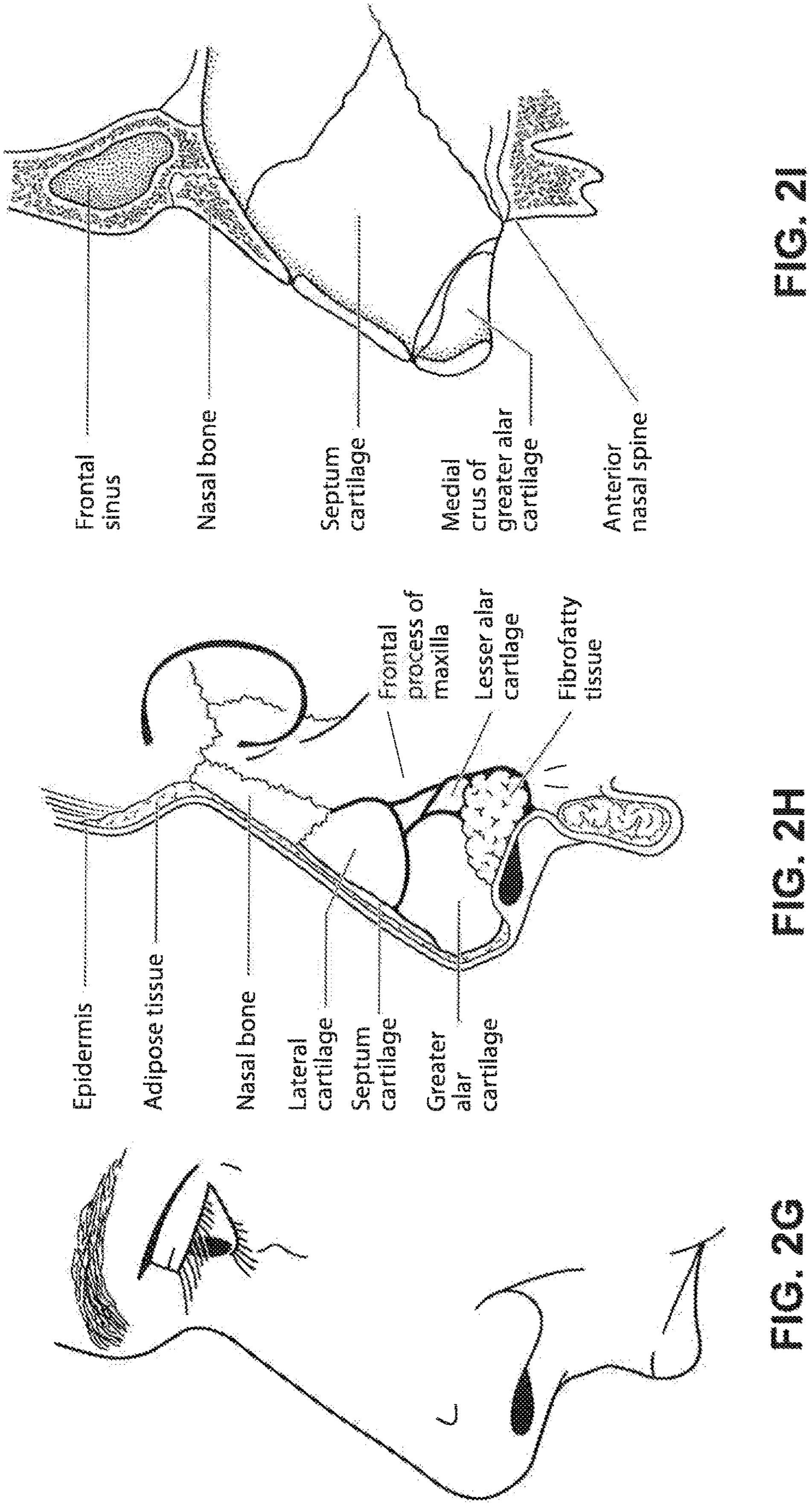

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
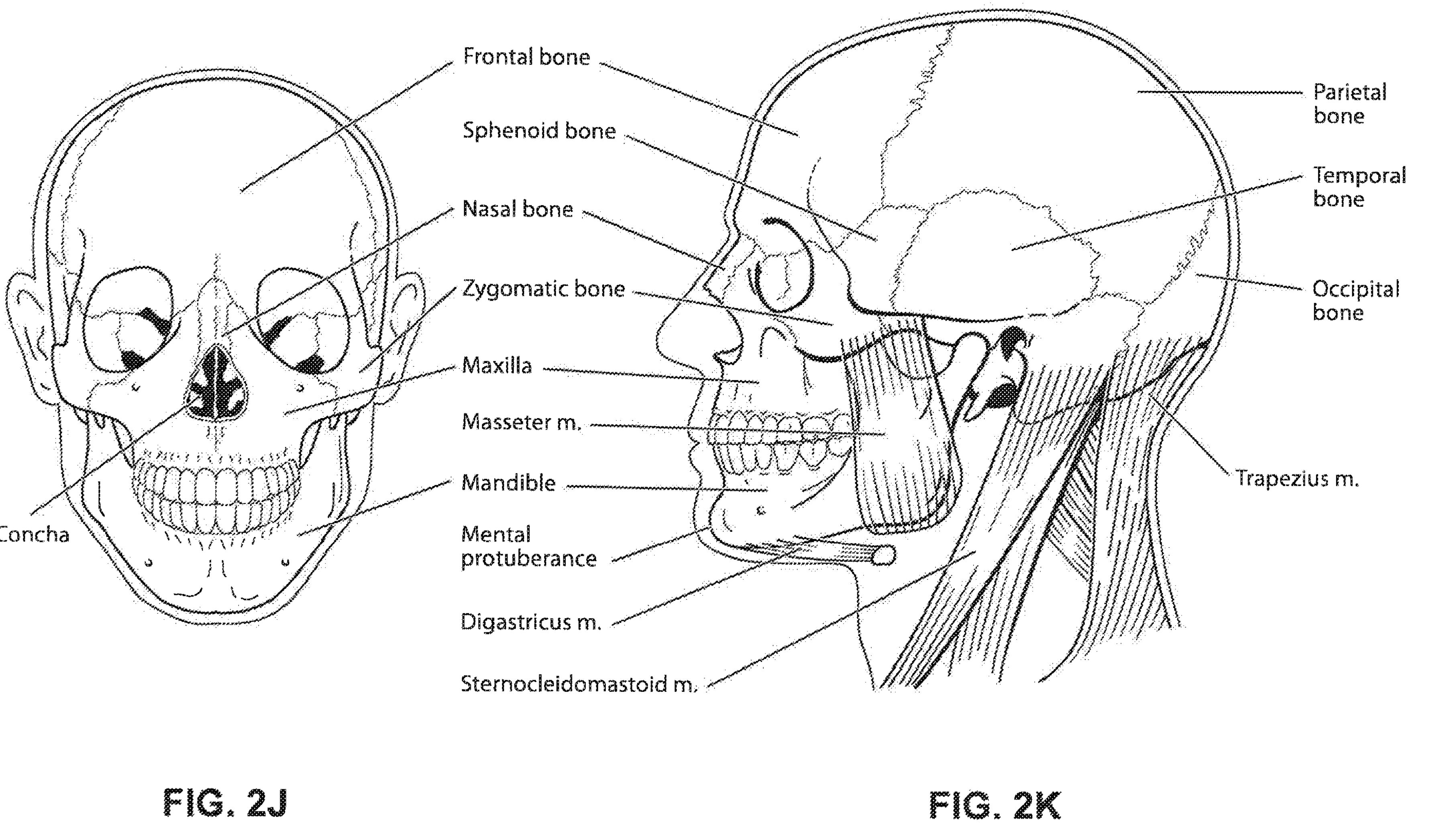

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
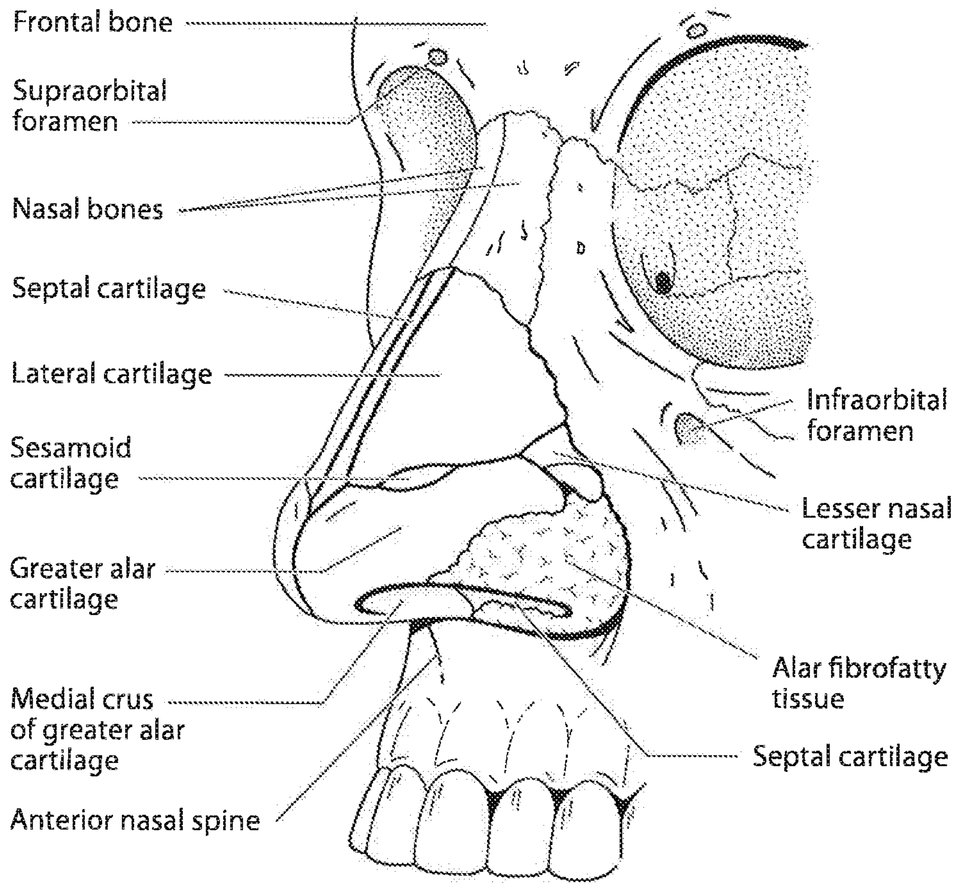

FIG. 2L shows an anterolateral view of a nose.

3.3 Patient Interface

Figure 3A:
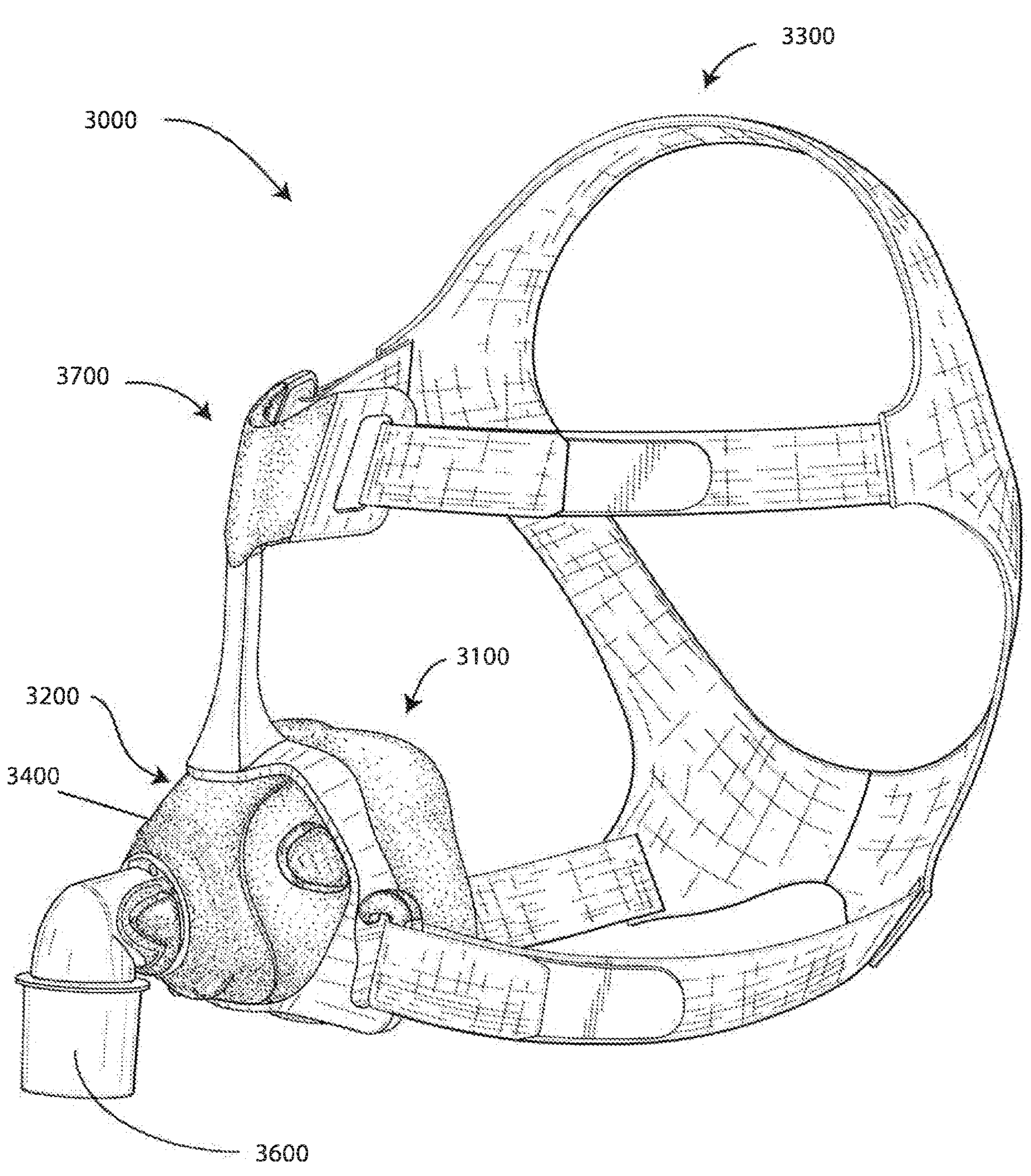

FIG. 3A shows a patient interface in the form of a nasal mask in accordance with one form of the present technology.

Figures 3B, 3C, 3D, 3E, 3F:
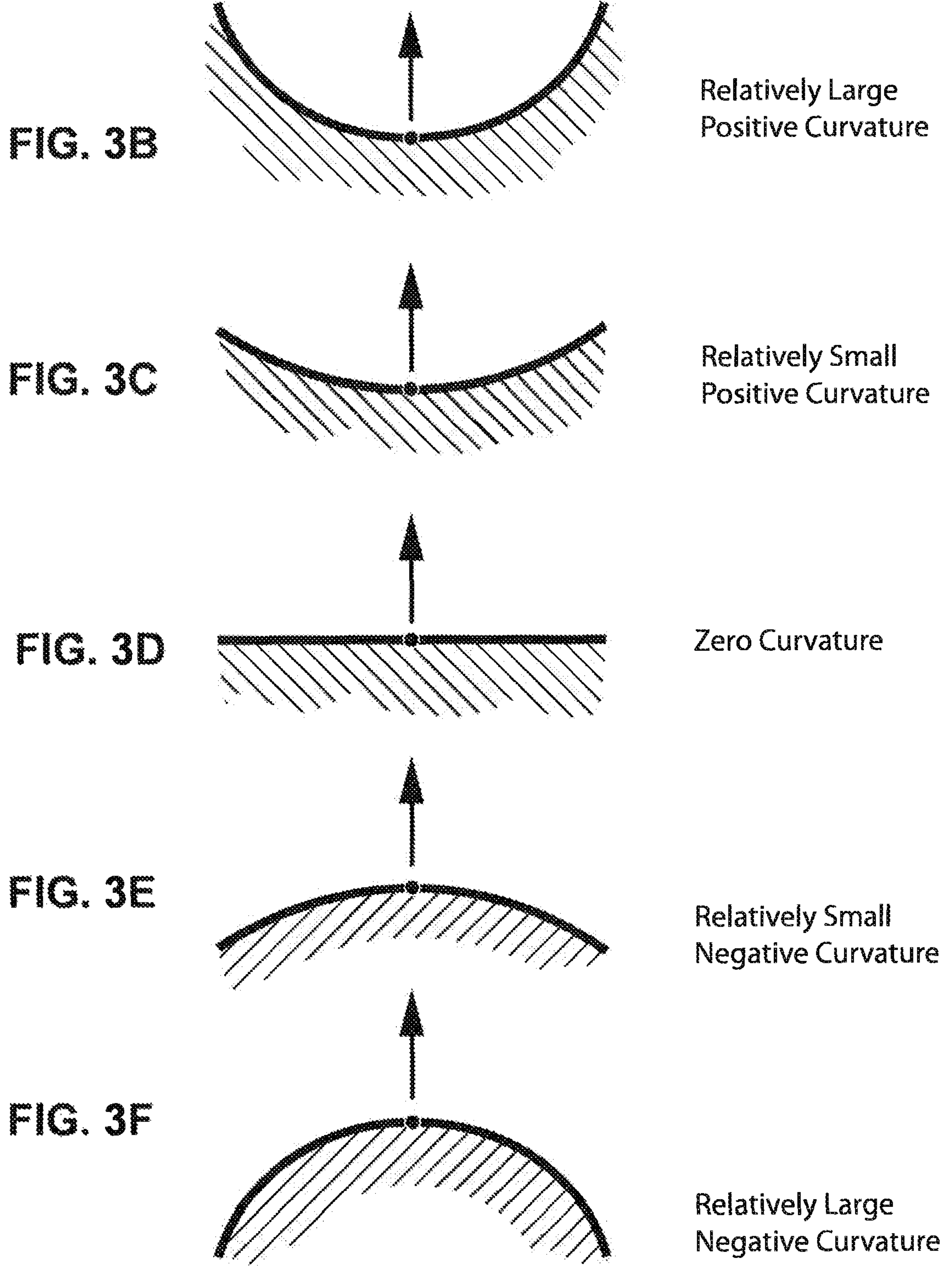

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figures 3G, 3H:
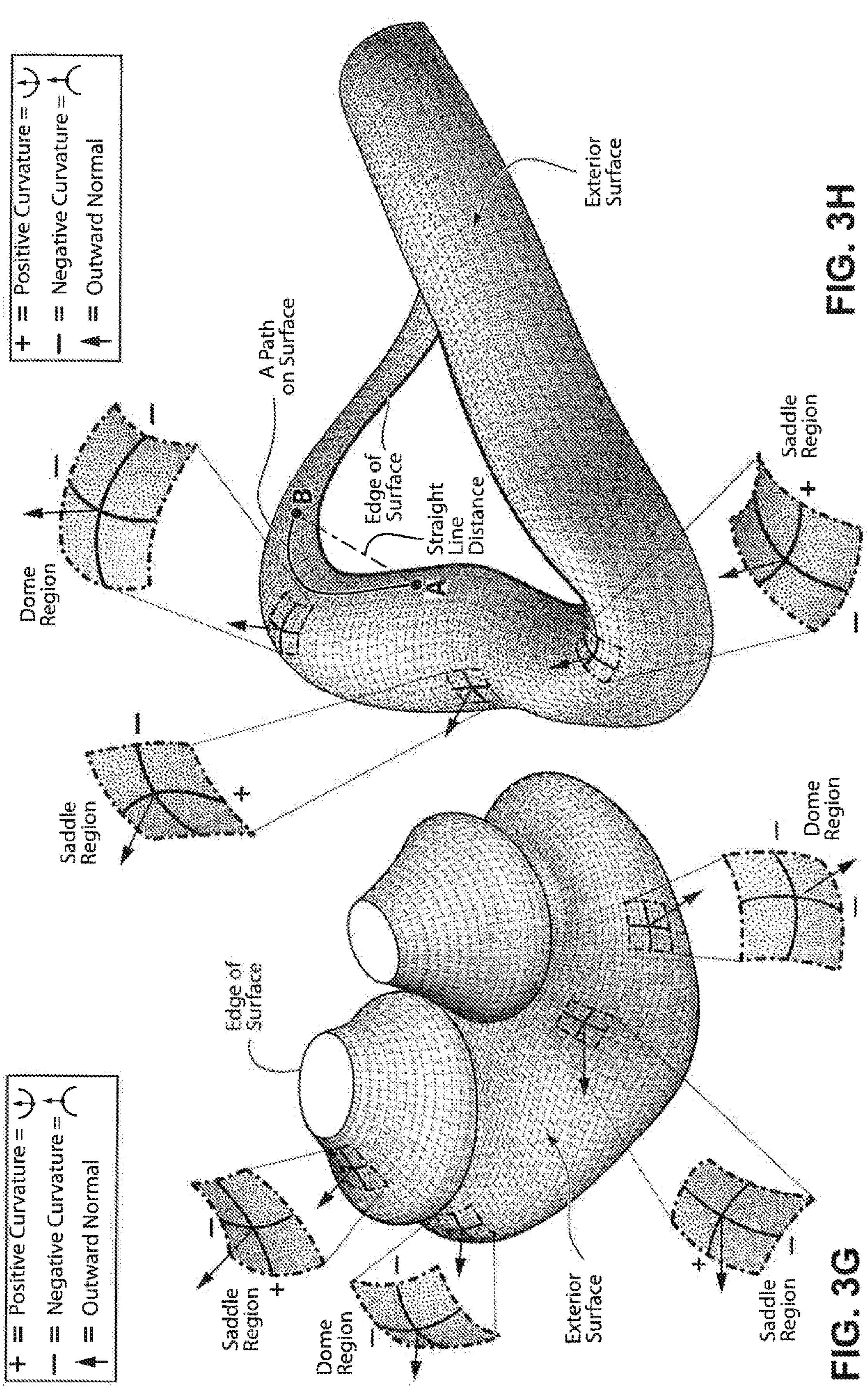

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figures 3I, 3J, 3K, 3L, 3M, 3N:
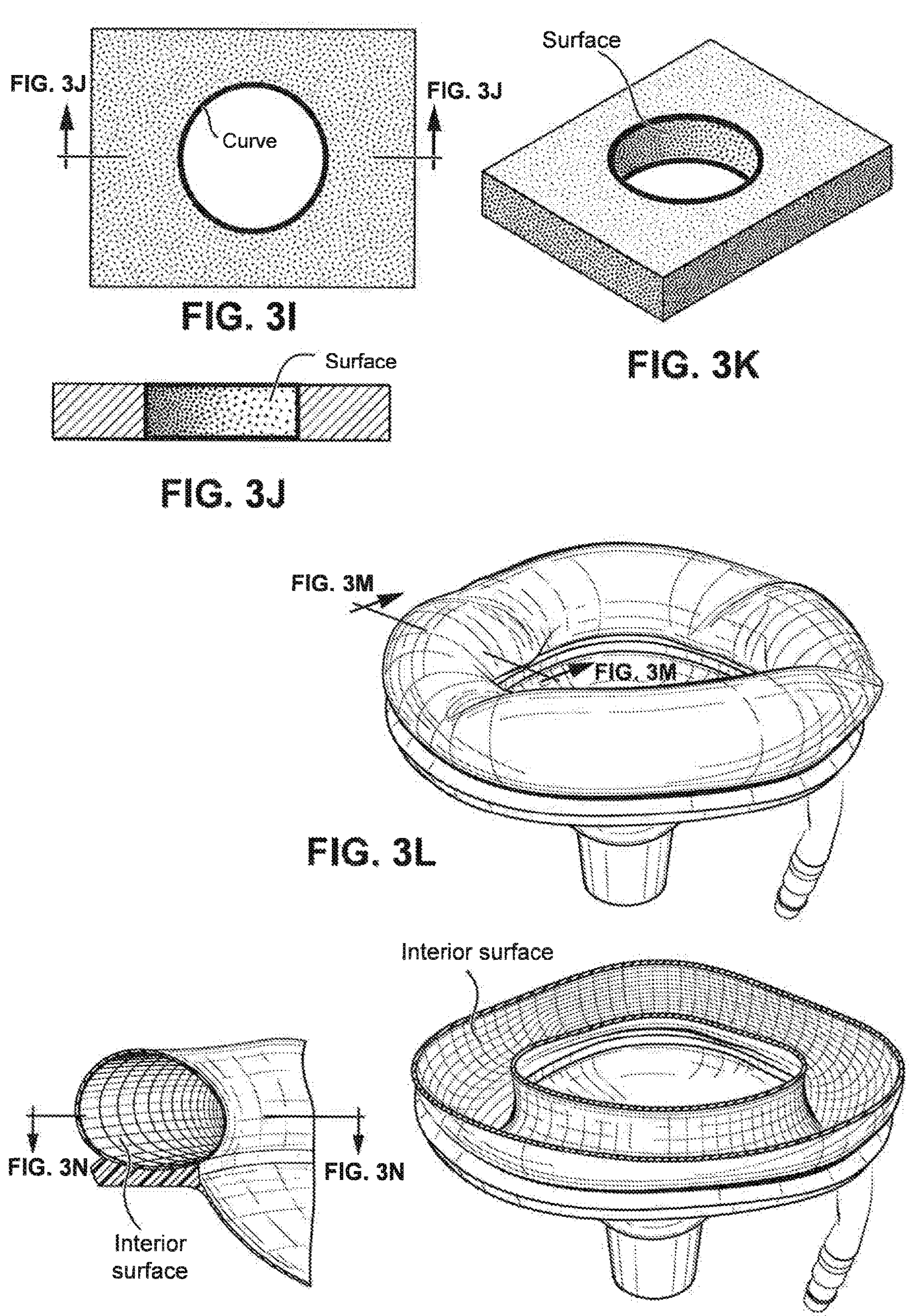

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figures 3U, 3V, 3W, 3X:
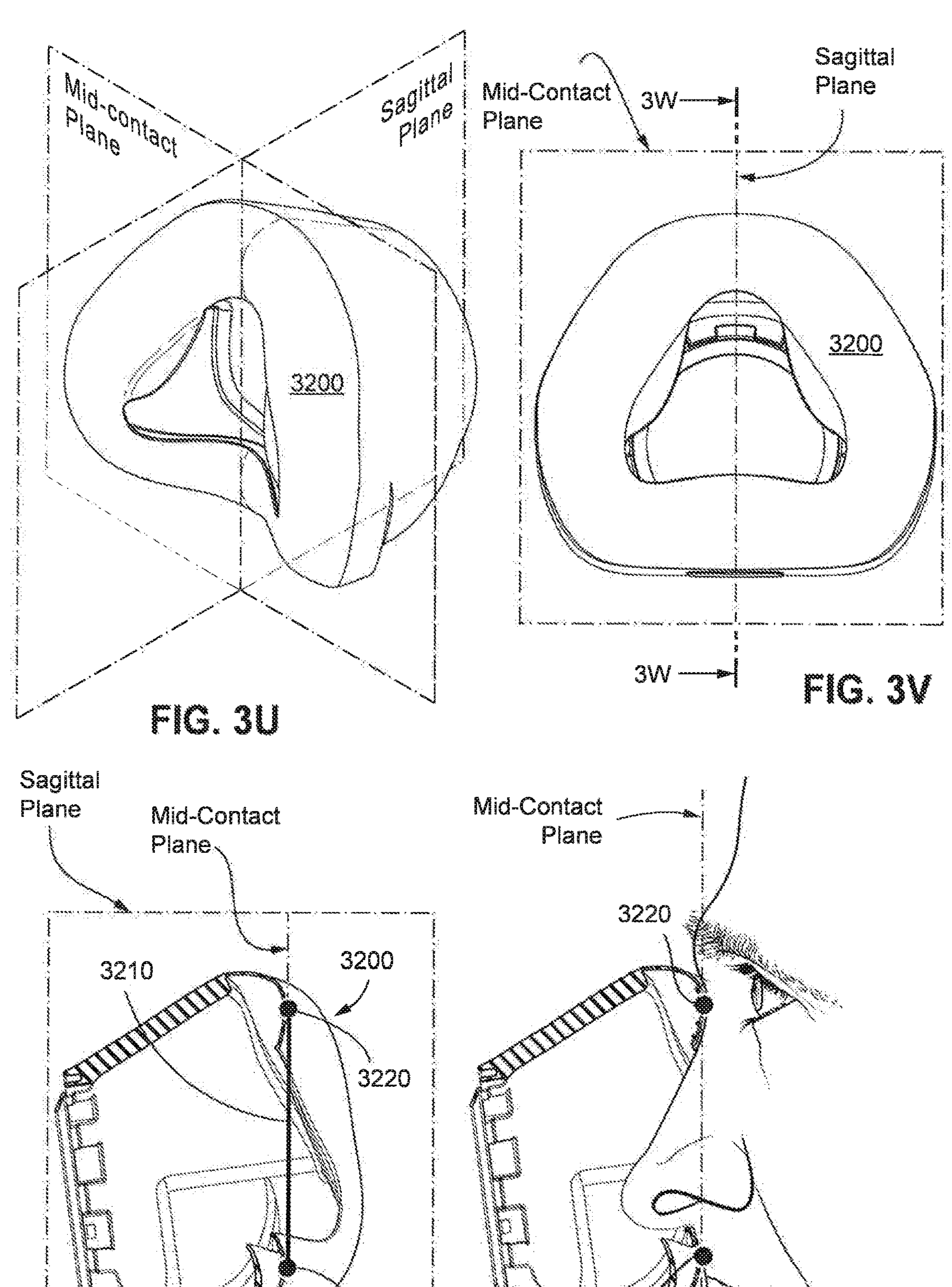

FIG. 3U shows a view of a plenum chamber 3200 showing a sagittal plane and a mid-contact plane.

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

Figure 3Y:
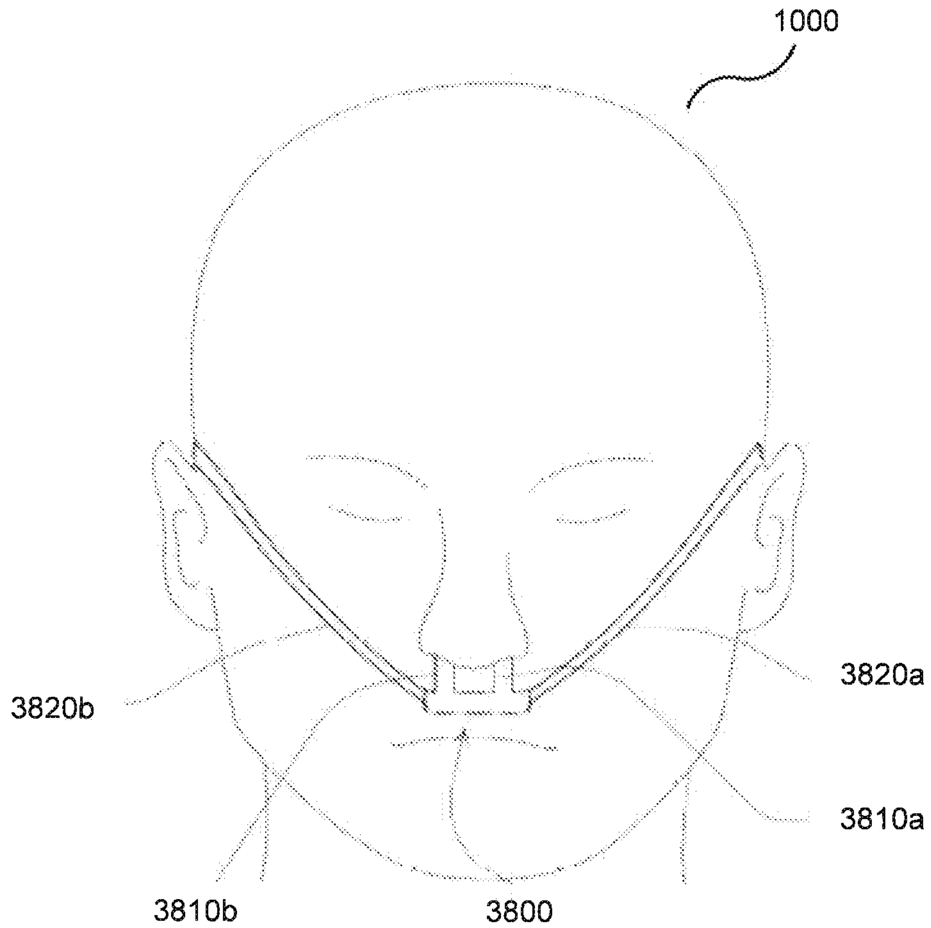

FIG. 3Y shows a patient interface in the form of a nasal cannula in accordance with one form of the present technology.

3.4 RPT Device

Figure 4A:
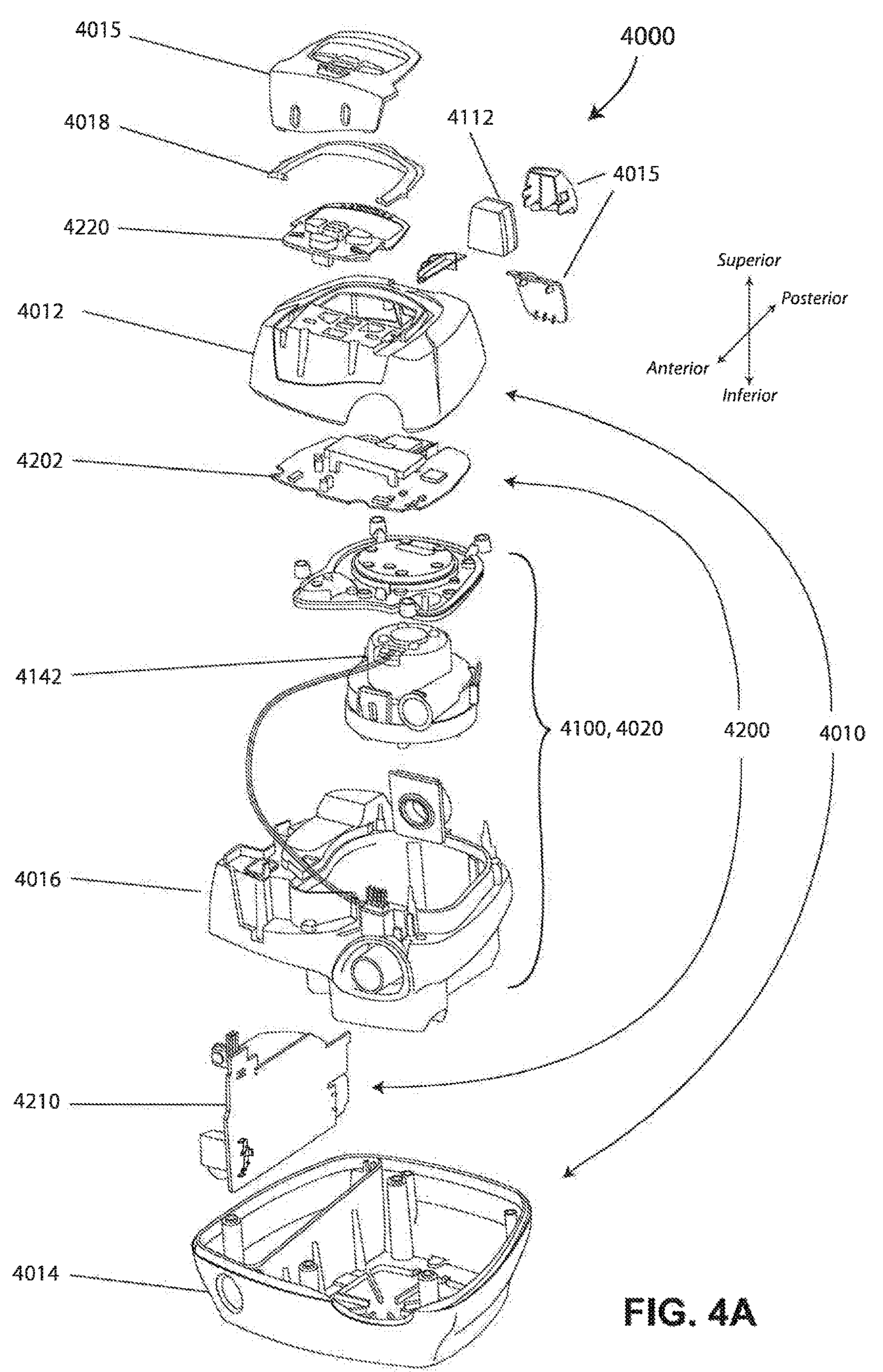

FIG. 4A shows an RPT device in accordance with one form of the present technology.

Figure 4B:
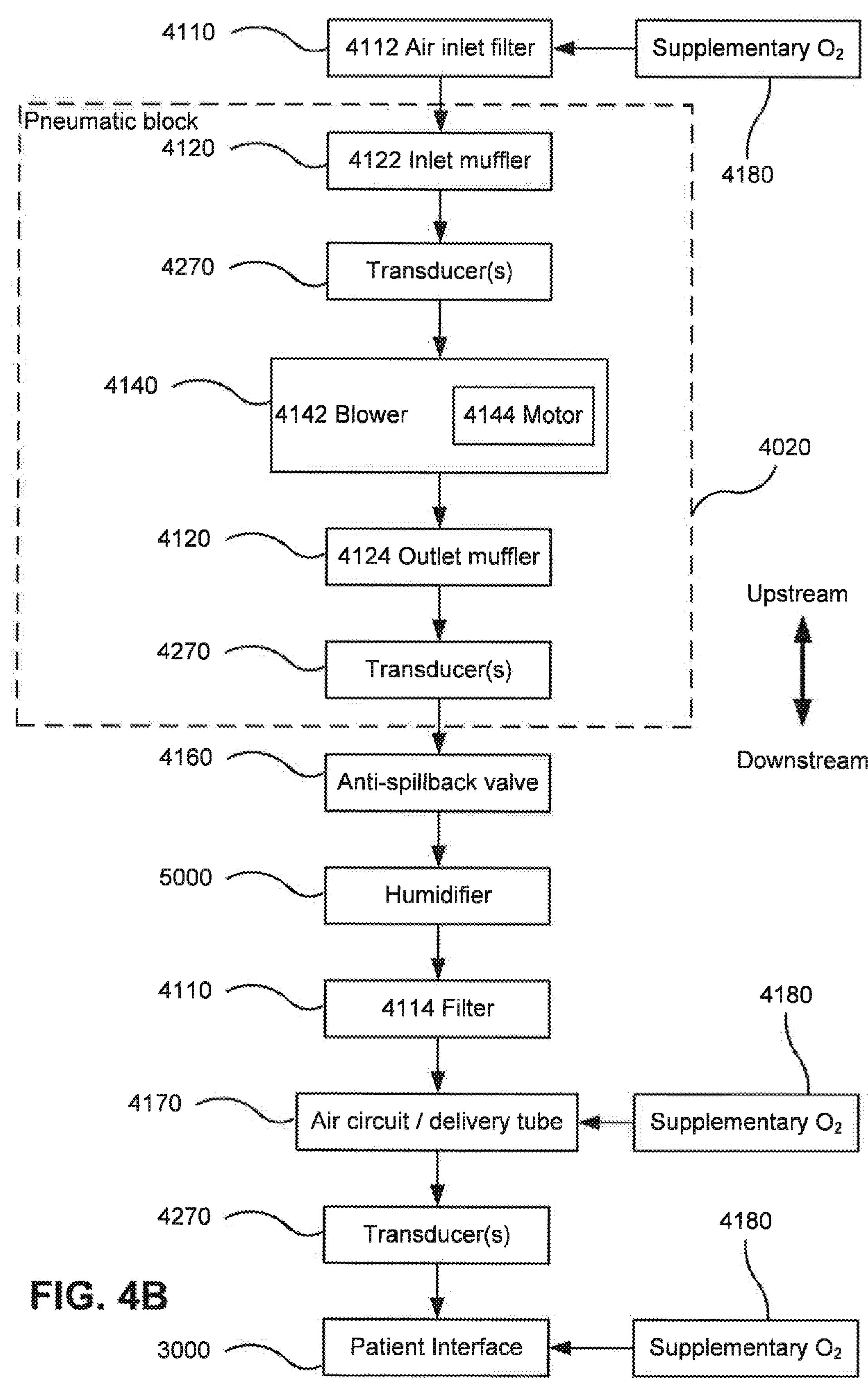

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

3.5 Humidifier

Figure 5A:
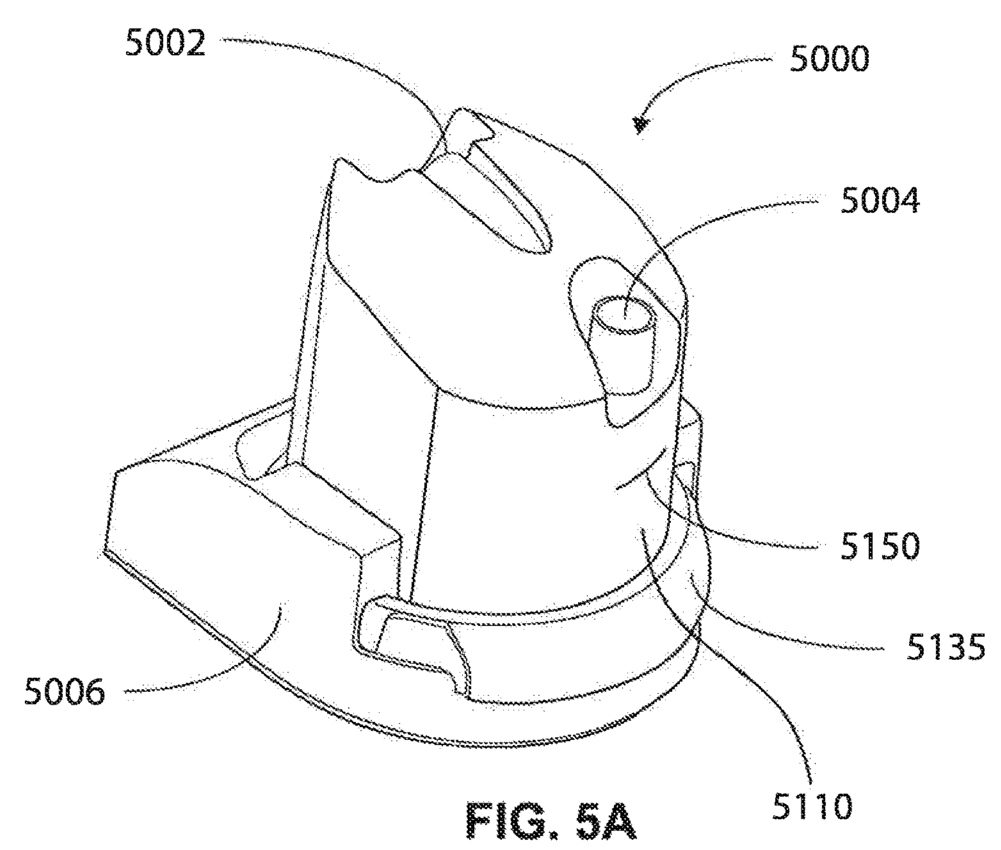

FIG. 5A shows an isometric view of a humidifier in accordance with one form of the present technology.

Figure 5B:
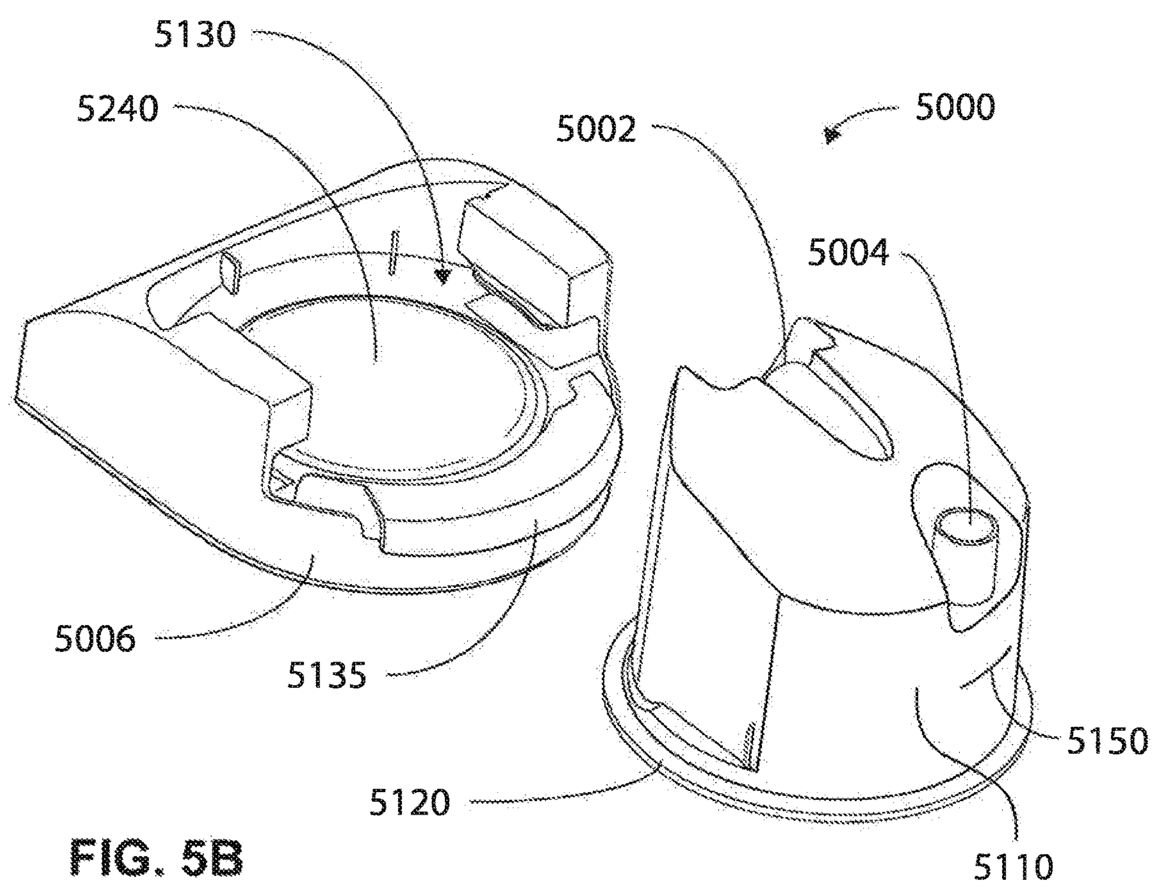

FIG. 5B shows an isometric view of a humidifier in accordance with one form of the present technology, showing a humidifier reservoir 5110 removed from the humidifier reservoir dock 5130.

3.6 Breathing Waveforms

Figure 6A:
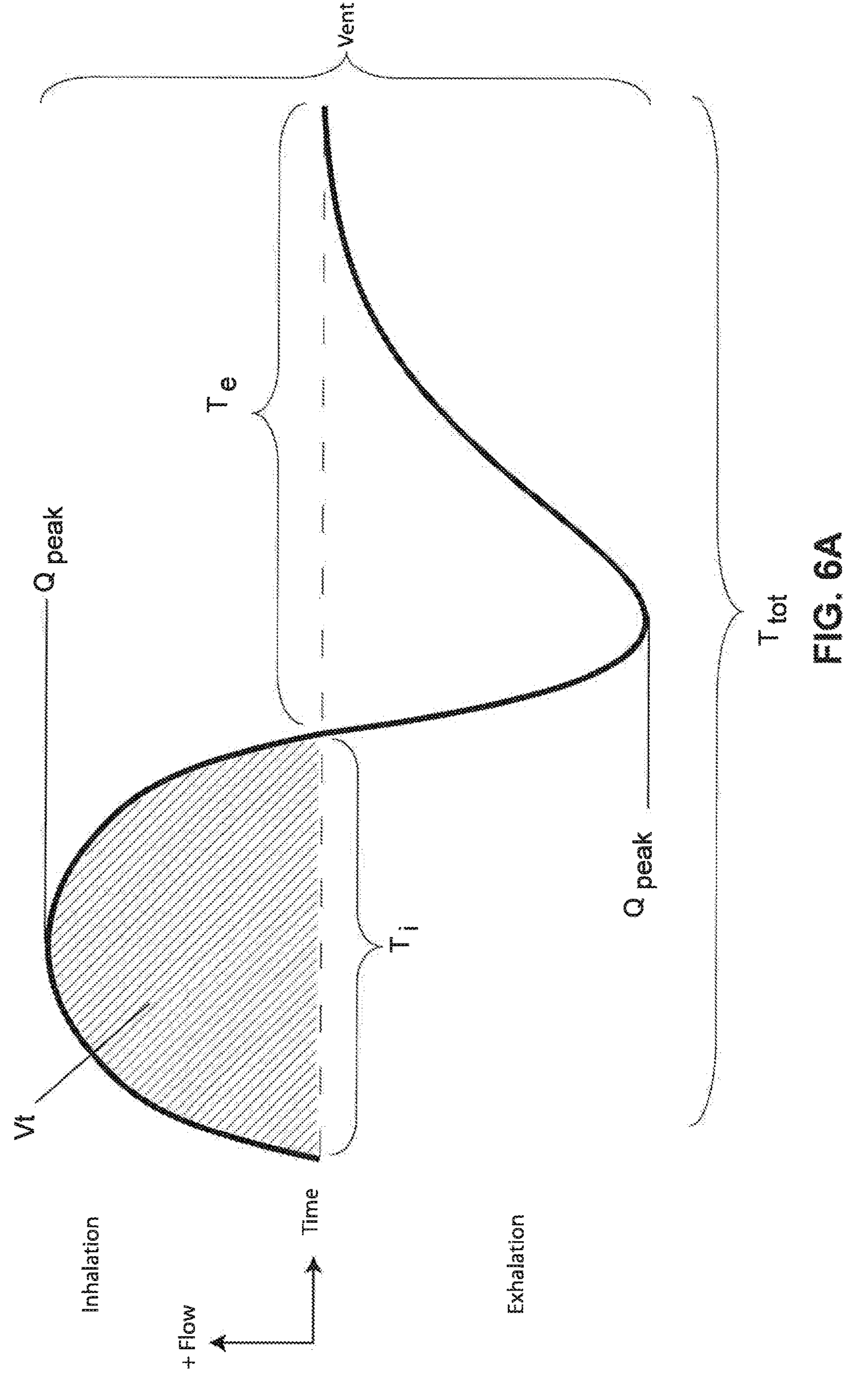

FIG. 6A shows a model typical breath waveform of a person while sleeping.

3.7 Patient Interfaces of the Present Technology

Figure 7A:
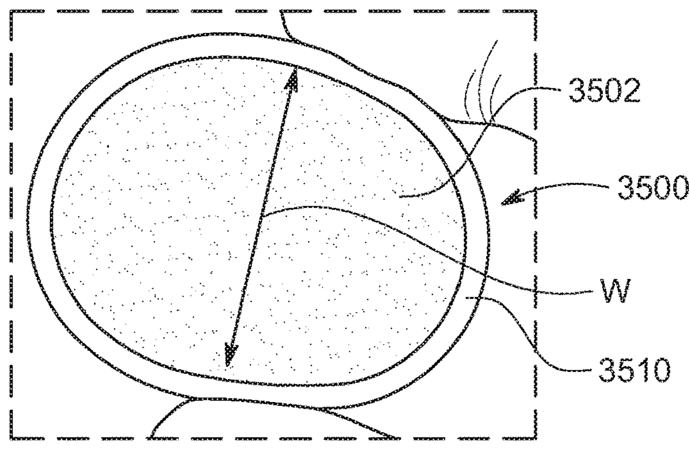

FIG. 7A shows an HME module according to one form of the technology.

Figure 7B:
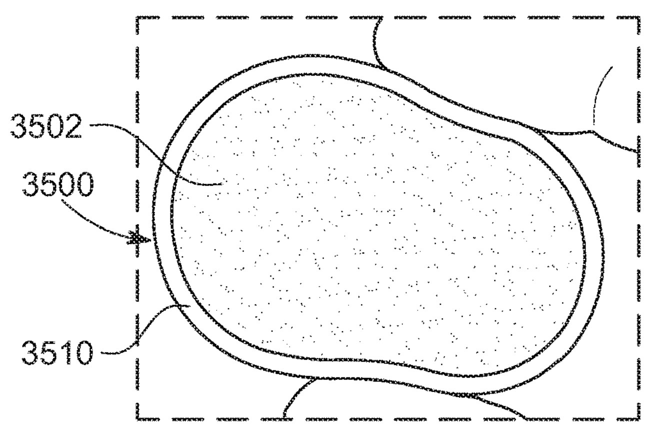

FIG. 7B shows the HME module of FIG. 7A being slightly compressed.

Figure 7C:
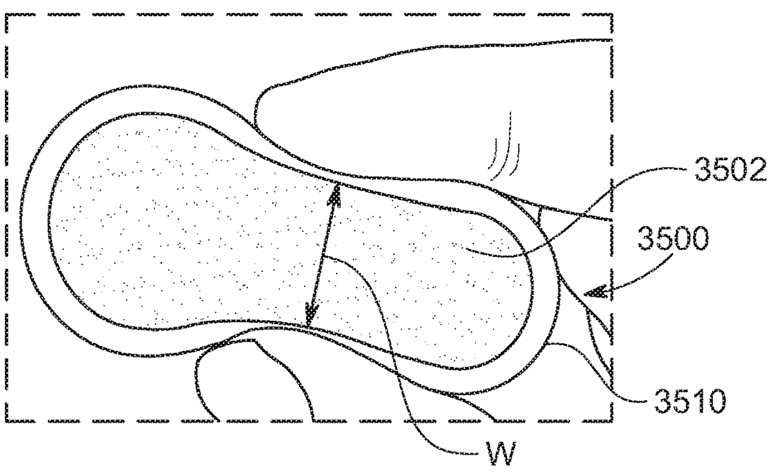

FIG. 7C shows the HME module of FIG. 7B being further deformed.

Figure 8:
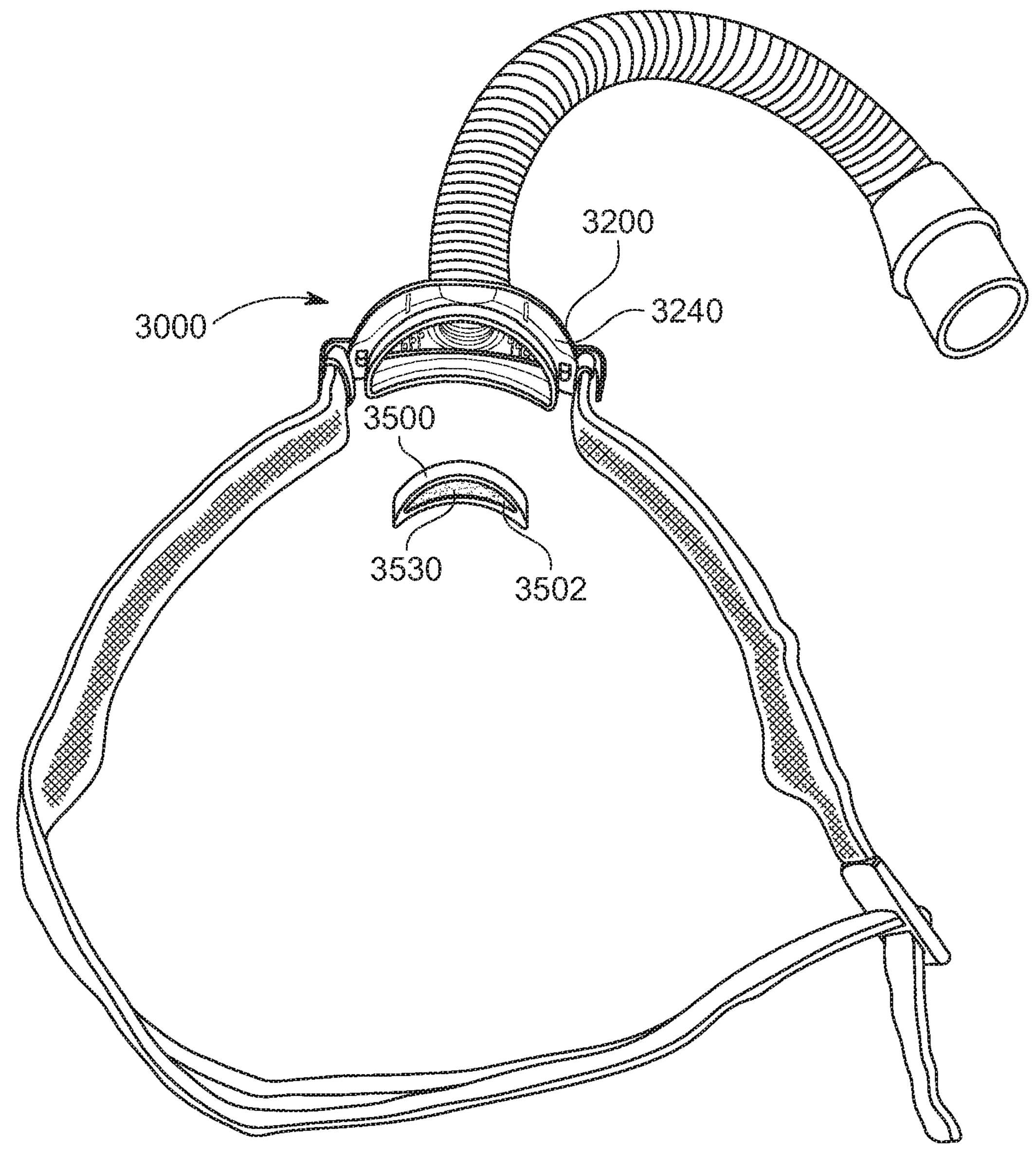

FIG. 8 shows a top perspective view of a patient interface according to one form of the technology, with a cushion module removed.

Figure 9:
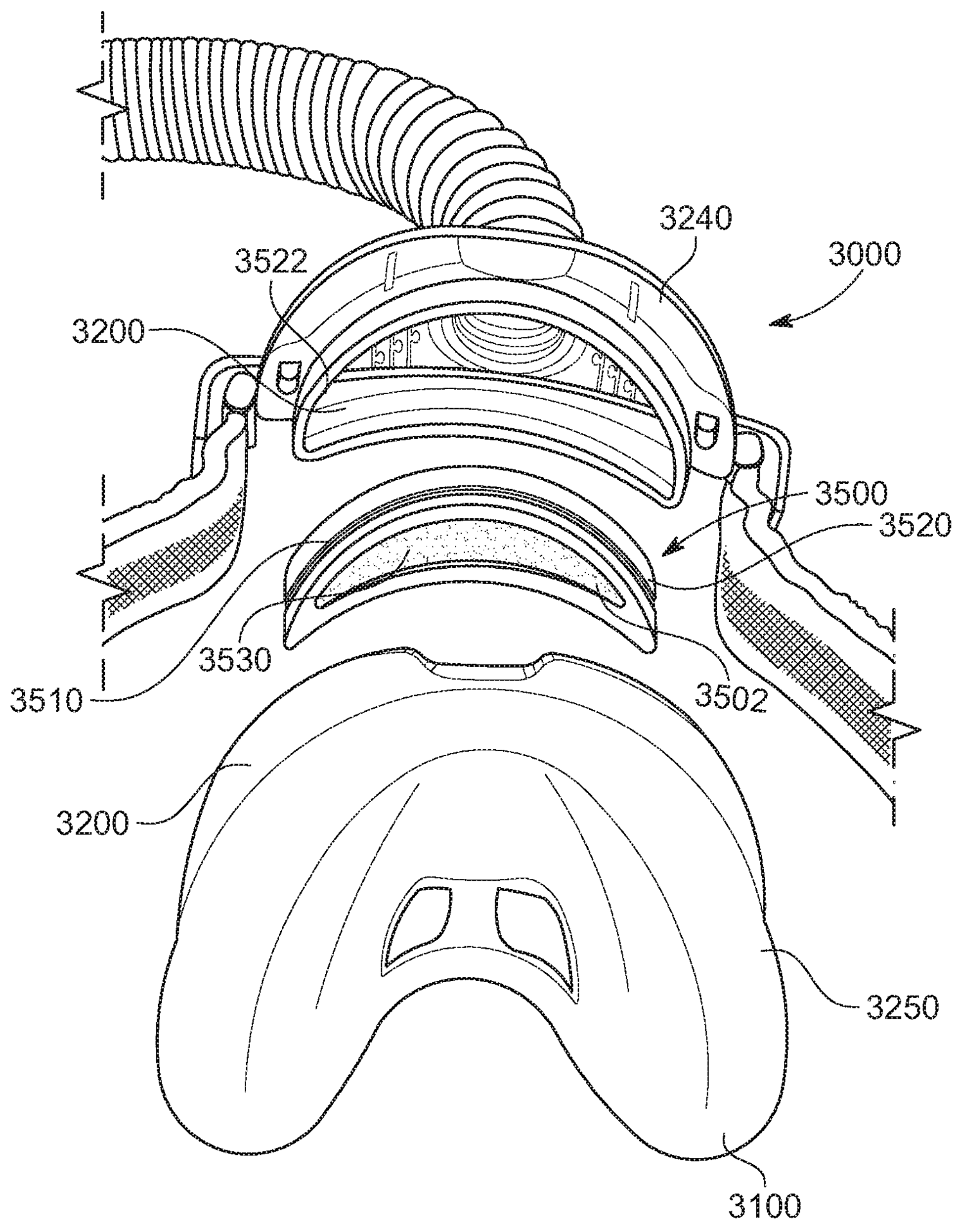

FIG. 9 shows an exploded view of the patient interface of FIG. 8.

Figure 10:
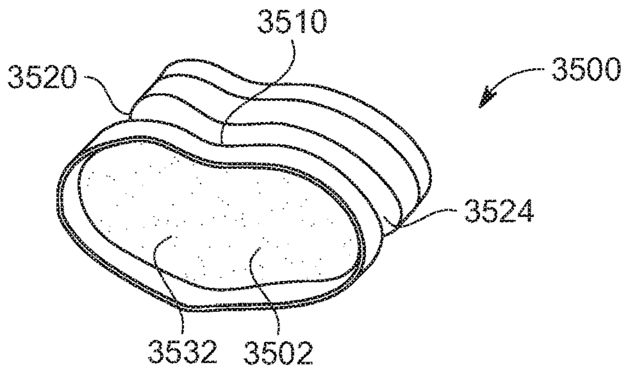

FIG. 10 shows a perspective view from a non patient facing side of one form of HME of the present technology.

Figure 11:
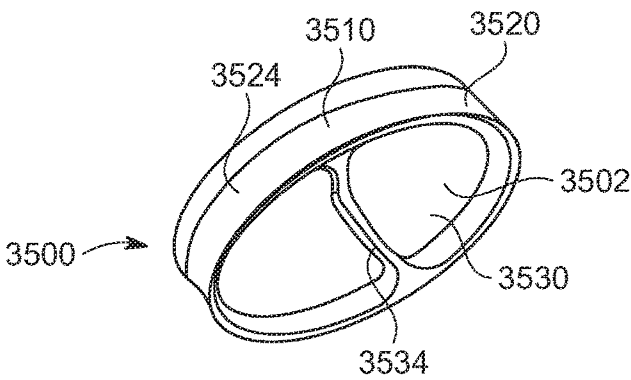

FIG. 11 shows a perspective view from a patient facing side of one form of HME of the present technology.

Figure 12:
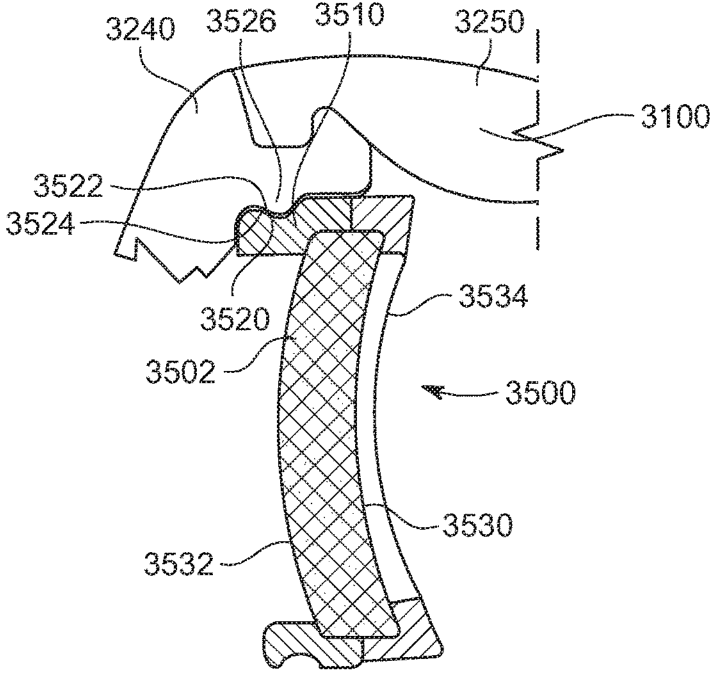

FIG. 12 is a partial diagrammatic cross-section of an HME of the present technology installed in a patient interface.

Figure 13:
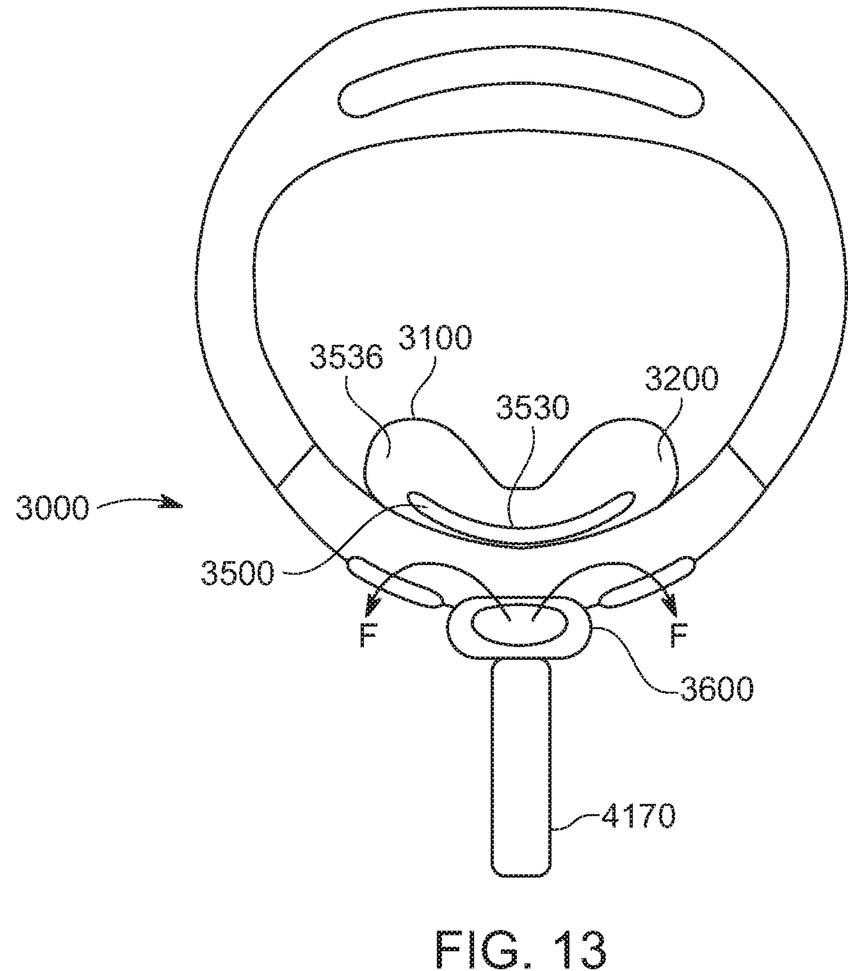

FIG. 13 is a diagrammatic view of a patient interface of the present technology.

Figure 14:
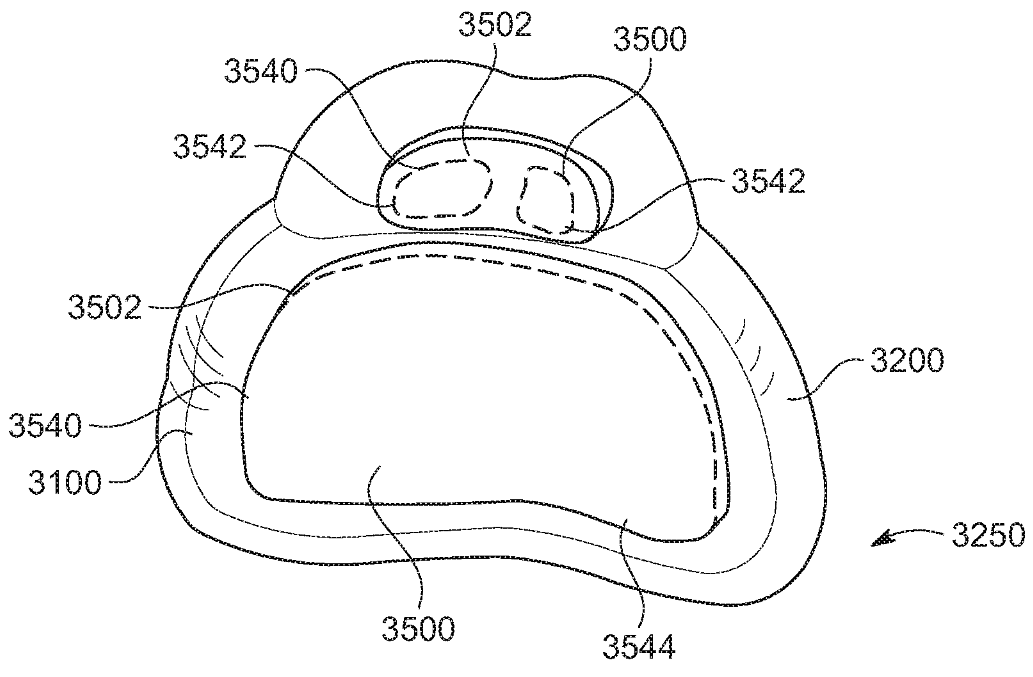

FIG. 14 is a diagrammatic front view of a cushion module of a patient interface according to one form of the technology, with holes in the seal forming structure shown in dashed lines.

Figure 15:
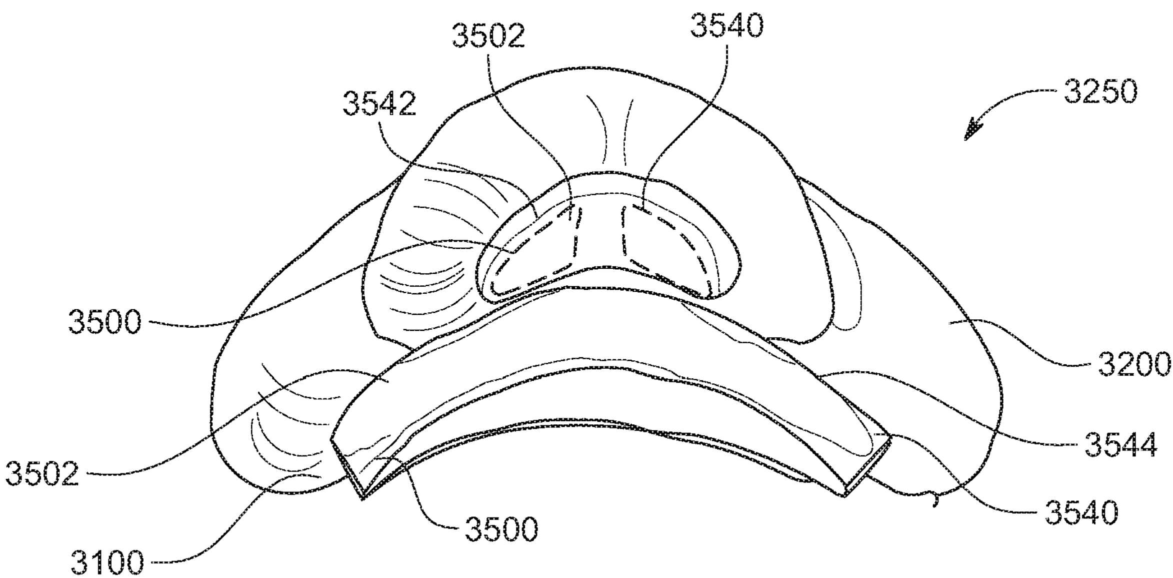

FIG. 15 is a diagrammatic top view of the cushion module of FIG. 14, with holes in the seal forming structure shown in dashed lines.

Figure 16:
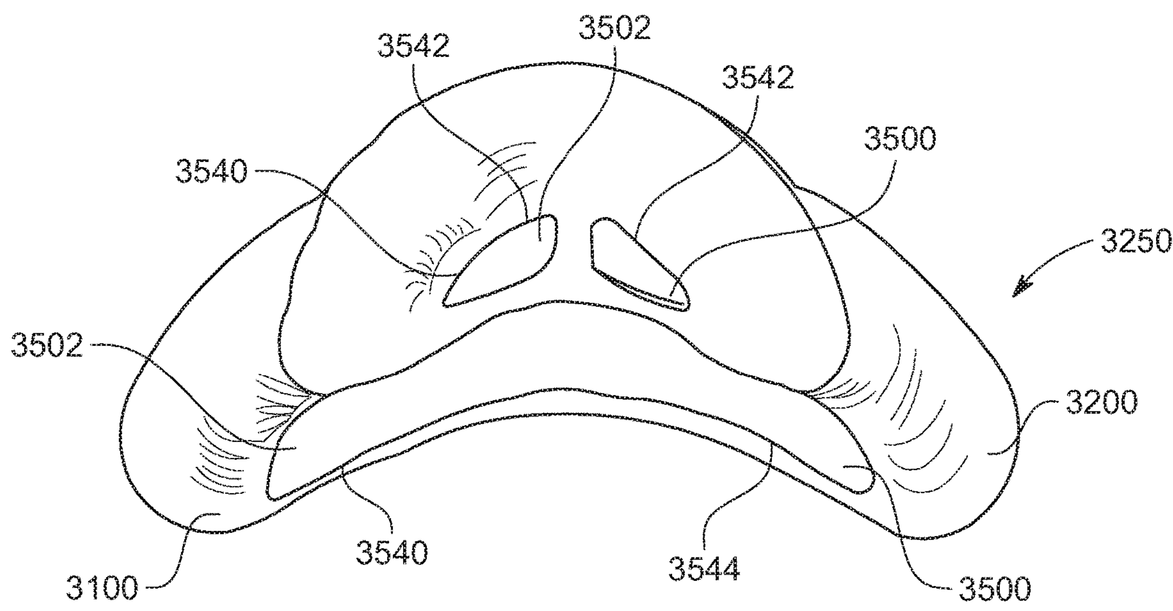

FIG. 16 is a diagrammatic top view of a cushion module of the patient interface according to one form of the technology.

Figure 17:
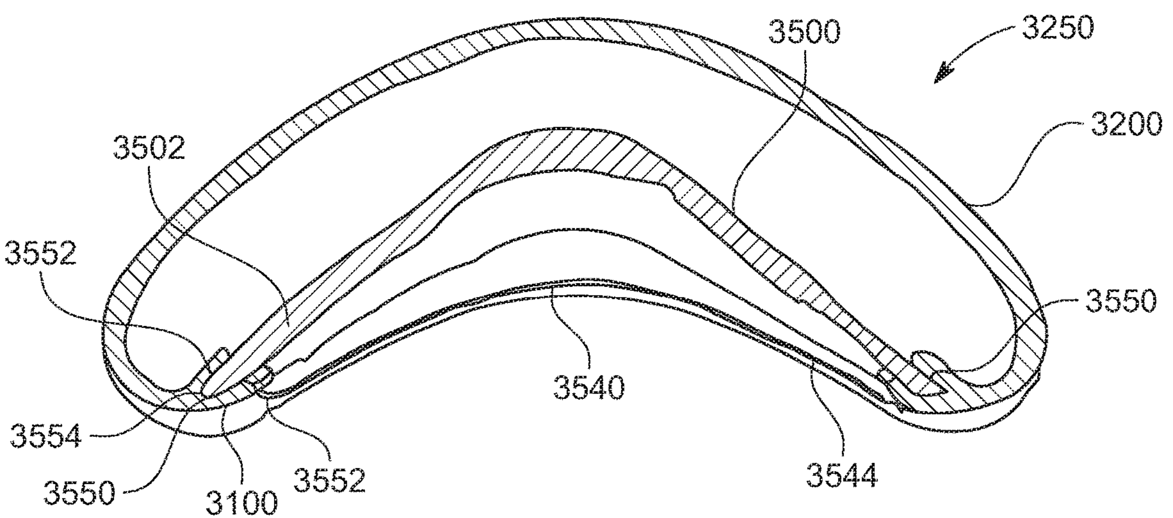

FIG. 17 is a diagrammatic cross-section through a cushion module according to another form of the technology.

Figure 18:
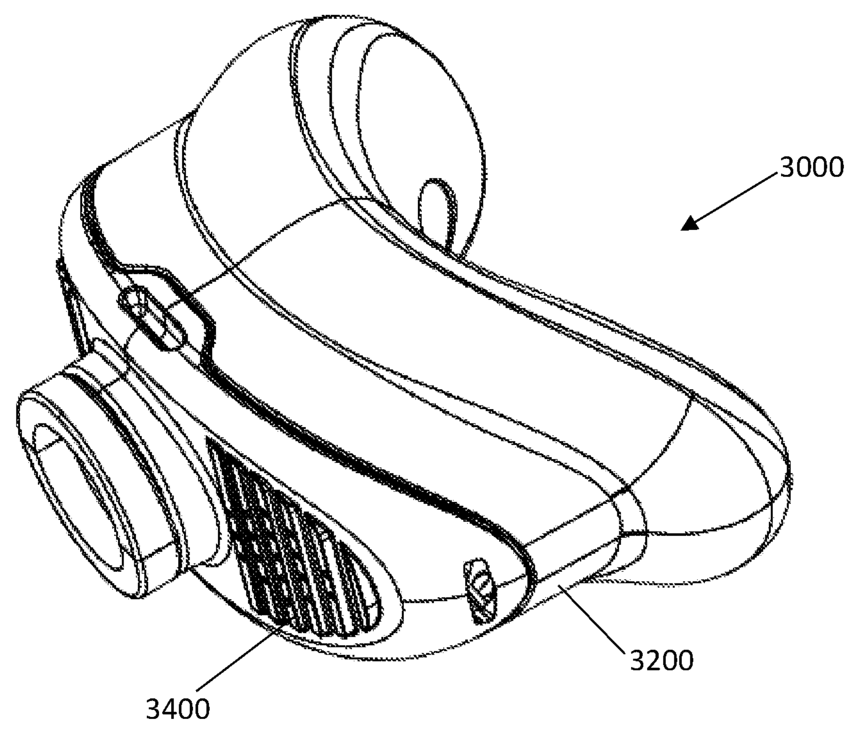

FIG. 18 is a top perspective view of a patient interface according to another form of the technology.

Figure 19:
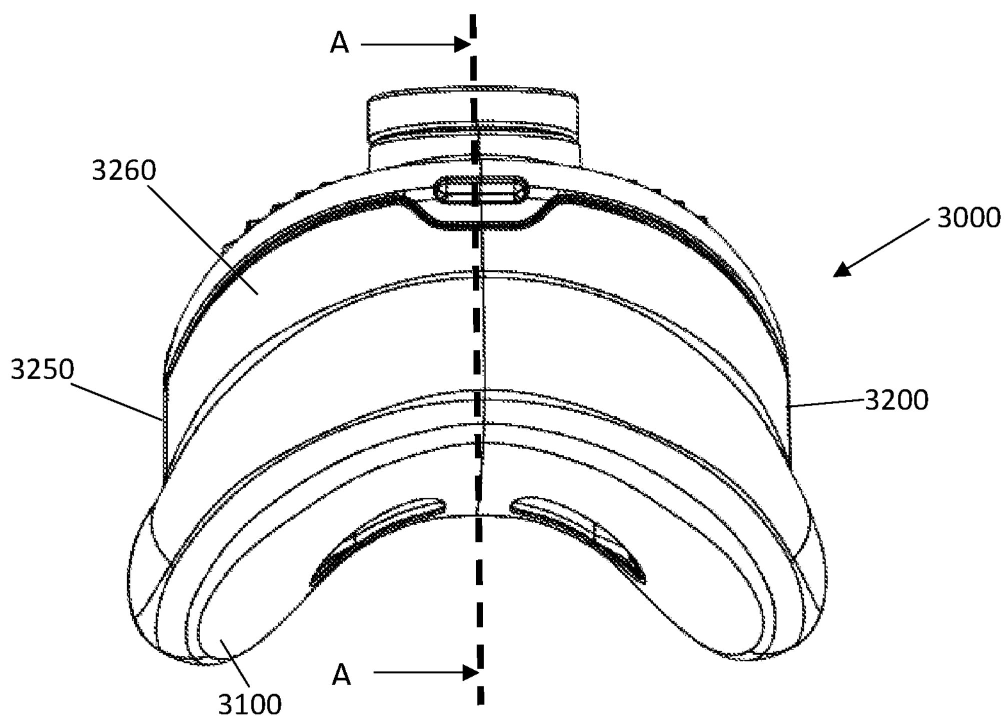

FIG. 19 is a top view of the patent interface of FIG. 18.

Figure 20:
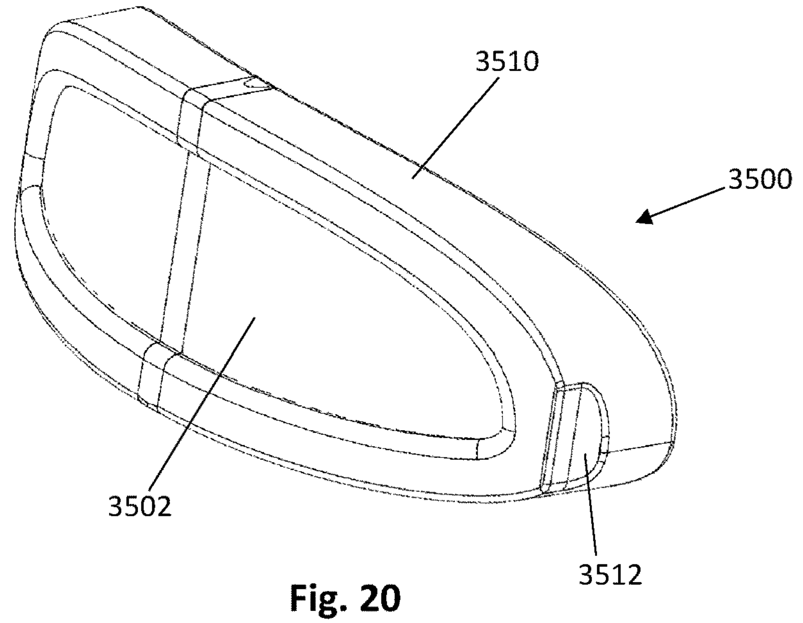

FIG. 20 is a top perspective view of an HME suitable for use with the patient interface of FIG. 18.

Figure 21:
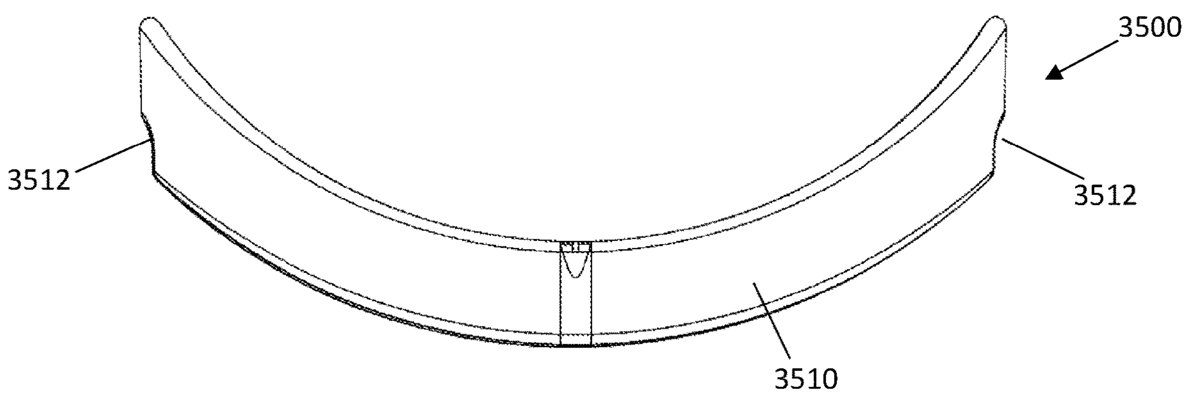

FIG. 21 is a top view of the HME of FIG. 20.

Figure 22:
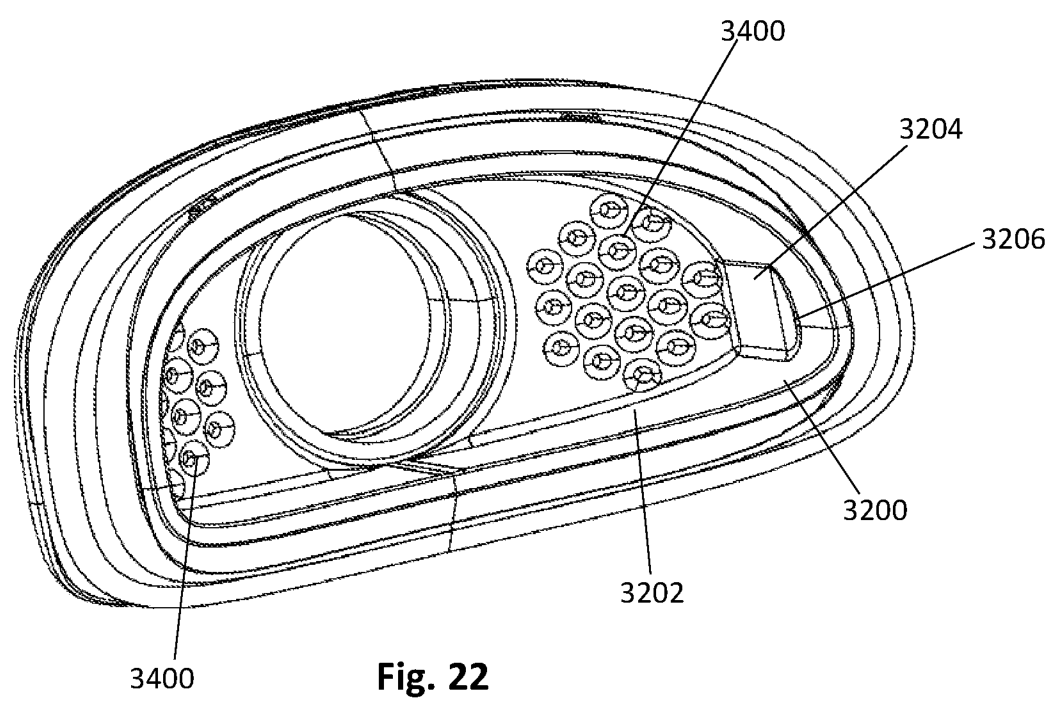

FIG. 22 is a rear perspective view of the patient interface of FIG. 18 with the cushion module and HME removed.

Figure 23:
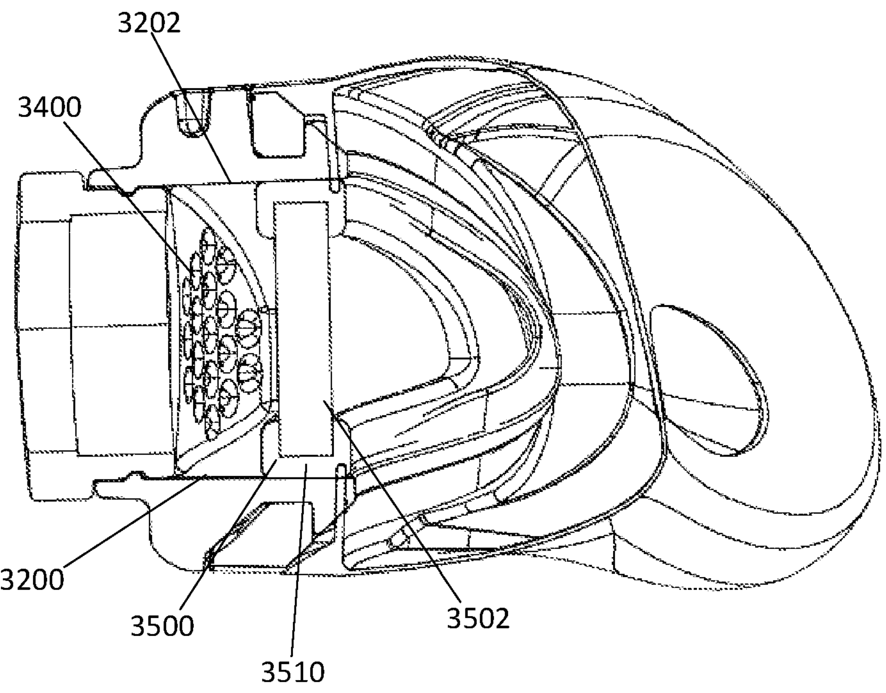

FIG. 23 is a cross-section through plane A-A.

Figure 24A:
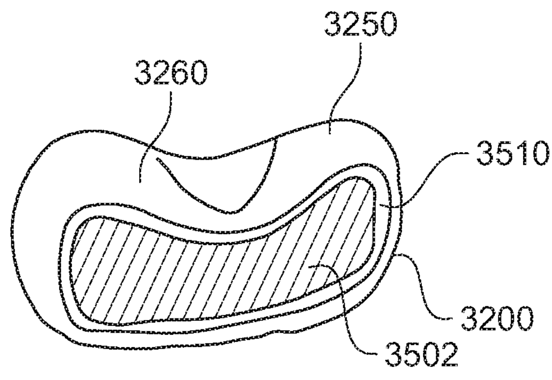

FIG. 24A shows a front perspective view of a cushion module of a patient interface according to another form of the technology, with an HME provided within the plenum chamber.

Figure 24B:
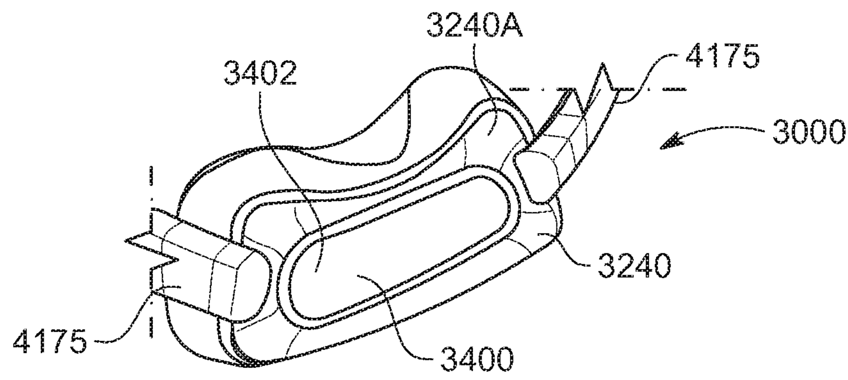

FIG. 24B shows a front perspective view of a patient interface comprising the plenum chamber and HME of FIG. 24A with a first frame attached to the cushion module.

Figure 24C:
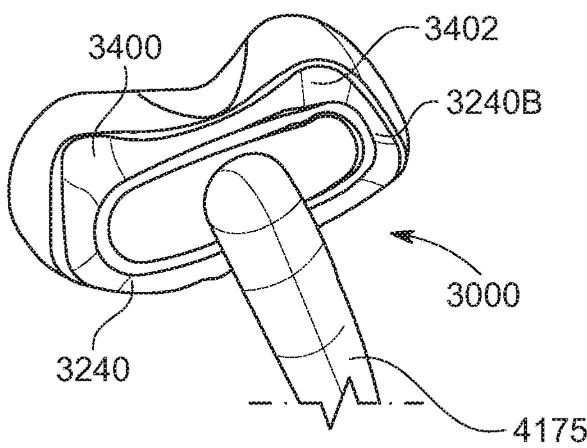

FIG. 24C shows a front perspective view of a patient interface comprising the plenum chamber and HME of FIG. 24A with a second frame attached to the cushion module.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000 or 3800.

4.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

An unsealed patient interface 3800, in the form of a nasal cannula, includes nasal prongs 3810*a*, 3810*b* which can deliver air to respective nares of the patient 1000 via respective orifices in their tips. Such nasal prongs do not generally form a seal with the inner or outer skin surface of the nares. This type of interface results in one or more gaps that are present in use by design (intentional) but they are typically not fixed in size such that they may vary unpredictably by movement during use. This can present a complex pneumatic variable for a respiratory therapy system when pneumatic control and/or assessment is implemented, unlike other types of mask-based respiratory therapy systems. The air to the nasal prongs may be delivered by one or more air supply lumens 3820*a*, 3820*b* that are coupled with the nasal cannula-type unsealed patient interface 3800. The lumens 3820*a*, 3820*b* lead from the nasal cannula-type unsealed patient interface 3800 to a respiratory therapy device via an air circuit. The unsealed patient interface 3800 is particularly suitable for delivery of flow therapies, in which the RPT device generates the flow of air at controlled flow rates rather than controlled pressures. The "vent" or gap at the unsealed patient interface 3800, through which excess airflow escapes to ambient, is the passage between the end of the prongs 3810*a* and 3810*b* of the nasal cannula-type unsealed patient interface 3800 via the patient's nares to atmosphere.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH2O with respect to ambient.

The patient interface 3000 in accordance with one form of the present technology is constructed and arranged to be able to provide a supply of air at a positive pressure of at least 10 cmH2O with respect to ambient.

The patient interface 3000 in accordance with one form of the present technology is constructed and arranged to be able to provide a supply of air at a positive pressure of at least 20 cmH2O (e.g. 30 cm H2O) with respect to ambient.

4.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

4.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. The support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

4.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

4.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

4.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

4.3.1.5 Forehead Region

In one form, the seal-forming structure that forms a seal in use on a forehead region of the patient's face. In such a form, the plenum chamber may cover the eyes in use.

4.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

4.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

In examples the patient interface may comprise a cushion module 3250 which defines the plenum chamber, at least in part. The cushion module 3250 may comprise the seal forming structure 3100 and, optionally, a shell 3260. In examples the cushion module may be connectable to a frame 3240. In examples the frame 3240 may also define part of the plenum chamber 3200.

4.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

4.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled CO2 by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

4.3.5 Decoupling Structure(s)

In one form the patient interface 3000 includes at least one decoupling structure, for example, a swivel or a ball and socket.

4.3.6 Connection Port

Connection port 3600 allows for connection to the air circuit 4170.

4.3.7 Forehead Support

In one form, the patient interface 3000 includes a forehead support 3700.

4.3.8 Anti-Asphyxia Valve

In one form, the patient interface 3000 includes an anti-asphyxia valve.

4.3.9 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

4.3.10 Heat and Moisture Exchanger (HME)

In accordance with one form of the present technology, a heat and moisture exchanger (HME) includes a heat and moisture exchanger (HME) module 3500. The HME module 3500 comprises a flexible heat and moisture exchange material 3502 and a retaining structure 3510. The flexible heat and moisture exchange material may include, for example, a foam or a non-woven material. Examples of suitable heat and moisture exchange material include HME7 foam, made by FoamPartner. The retaining structure 3510 is provided around an outer perimeter of the flexible heat and moisture exchange material 3502. In examples, the retaining structure is configured to maintain the HME module 3500 in a required position within the plenum chamber of a patient interface, in use.

Some foam HME materials may have a number of advantages over the paper HME materials of the prior art. For example the impedance to air flowing through the foam may be substantially the same, regardless of the direction of the air flow. By contrast, fluted paper HME material may have a higher impedance to air flows which are not aligned with the flutes than it does to air flows which are aligned. Furthermore, some foam HME materials may be washable. Foam HME materials may also allow overmoulding of features over the HME material. Foam HME materials may also be more compliant than some paper HMEs, which may allow them to deform when the patient interface deforms, in use.

In other examples the HME material may comprise a non-woven fabric. Non-wovens may have similar advantages to those listed above in respect of foam HME materials. Other suitable flexible heat and moisture exchange material may also be used.

The retaining structure 3510 may be formed of a flexible/pliable material, for example a silicone or thermoplastic elastomer (TPE). Alternatively, the retaining structure may be formed of a stiffer or more rigid material. The use of a flexible or rigid retaining structure may depend on design requirements or applications, for example on the stiffness or flexibility of the walls of the plenum chamber of the interface which the HME is intended for use with. In examples intended for use with a patient interface which has relatively flexible plenum chamber walls, the stiffness of the retaining structure may be selected to ensure that the plenum chamber retains the required degree of flexibility when the HME is installed.

FIGS. 7A and 7B show different views of a heat and moisture exchanger (HME) module 3500 in accordance with one form of the present technology. The HME module comprises a flexible heat and moisture exchange material 3502 and a retaining structure 3510. In examples, the retaining structure 3510 is formed from a flexible/pliable material that is provided around an outer perimeter of the flexible heat and moisture exchange material 3502. The flexible heat and moisture material together with the retaining structure 3510 forms a HME module 3500 that is resiliently flexible. This allows the HME module to flex easily when a force is applied to the HME module, as shown in FIG. 7C. In examples, the flexibility of the HME module 3500 allows it to easily conform to a shape of an interior of a cushion module or plenum chamber of a patient interface. Such a flexible configuration may allow a one-size HME module to be used with different size cushion modules of a patient interface and/or with a range of different patient interfaces having different shape cushion modules. In examples, the HME has a width dimension, measured transverse to the direction of fluid flow through the HME in use, and the HME is sufficiently flexible that it can be deformed to 50% of its original width without plastic deformation, as shown in FIG. 7C.

Referring next to FIGS. 8 and 9, a patient interface 3000 in accordance with one form of the present technology comprises a heat and moisture exchanger (also known as an HMX or HME) 3500 provided within the plenum chamber 3200. In examples the plenum chamber 3200 is defined in part by a frame 3240.

In one form of the technology the HME 3500 comprises a flexible heat and moisture exchange material 3502. In examples, a retaining structure 3510, formed from a pliable material, for example a flexible thermoplastic, is formed around an outer perimeter of the heat and moisture exchange material 3502, for example by overmoulding.

In examples, the retaining structure 3510 is configured to be engaged within the plenum chamber 3200 in a snap fit. The retaining structure 3510 may comprise one more snap fit features 3520 which engage one or more complementary snap fit features 3522 provided within the plenum chamber 3200. In the examples shown in FIGS. 10 to 12, snap fit feature 3520 comprises a channel 3524 which extends around the entire circumference of the retaining structure 3510. A snap fit retaining member comprising a rib 3526 with a complementary shape to the channel 3524 is provided within the plenum chamber. In examples the rib 3526 is provided to the frame 3240.

In use, the rib 3526 engages the channel 3524 to hold the HME 3500 in position inside the plenum chamber 3200. In examples the HME 3500 is installed from the patient facing side of the patent interface 3000, e.g. by removing the seal forming structure and/or cushion module 3250 and inserting the HME 3500 into the plenum chamber 3200, rather than inserting the HME 3500 into the plenum chamber from the non-patient facing side of the patient interface 3000.

In some examples the channel 3524 may extend around the entire perimeter of the retaining structure 3510, although in other examples the channel 3524 may not extend around the entire perimeter. In examples more than one channel 3524 may be provided around the perimeter of the retaining structure 3510. More than one rib 3526 may also be provided.

In examples, the heat and moisture exchange material 3502 has a first face 3530 on a patient facing side of the HME 3500 and a second face 3532 on a non patient facing side of the HME 3500. In examples, the retaining structure 3510 does not extend over the patient facing side of the heat and moisture exchange material 3502 or the non patient facing side of the heat and moisture exchange material 3502. However, in other examples the retaining structure 3510 may comprise a shaping member 3534 which extends across the first face 3530, for example as shown in FIGS. 11 and 12. The shaping member 3534 may have a concave shape (as viewed from the patient side), and may be configured to impart a concave shape to at least the first face 3530. In some examples the shaping member 3534 may bend the HME material 3502 such that the second face 3532 is convex, as shown in FIG. 12. In some examples the heat and moisture exchange material 3502 may be shaped and configured to have a concave first face 3530 when no external force is applied to the first face 3530. The shaping member 3534 may also function to help retain the HME material 3502 within the retaining structure. In examples, this may be the only function of the member.

To ensure the patient receives the most benefit from the HME 3500, it may be important that most of the breathable gas inspired by the patient has passed through the HME 3500 and that most of the gas expired by the patient passes through the HME 3500 before being vented to atmosphere. In examples, the patient interface 3000 is configured such that the HME 3500 provides at least 10 mg/L humidification (i.e. each litre of breathable gas passing through the HME 3500 to the patient has at least 10 mg of water added to it). In the example shown in FIGS. 7-9 the HME has a volume of at least 1500 mm3. Other values with respect to the humidification and volume of the HME may also be useful, depending on the design of the HME and the heat and moisture exchange material.

Examples of the technology may be configured to reduce the volume 3536 (see FIG. 13) in the plenum chamber 3200 on the patient side of the HME 3500 (e.g. the volume between the entrance to the patient's airways and the patient facing side of the HME 3500, i.e. interface deadspace). Reducing interface deadspace volume 3536 may assist in reducing rebreathing of CO2.

In some forms of the technology the HME 3500 is positioned in the plenum chamber 3200 such that breathable gas entering the patient interface 3000 through the connection port(s) 3600 can flow to the vent(s) 3400 without passing through the HME 3500, as indicated by arrows F in FIG. 13. In this way, venting of gas from the RPT which has not been inspired by the patient (for example during breath pause between inhalation and exhalation) does not remove moisture from the HME 3500.

In examples, the plenum chamber 3200 is formed from one or more flexible materials, that is, it is able to deform under the loads experienced during normal use while the patient is receiving therapy, in particular loads created when the patient lies on their side with their head on a pillow. In one form of the technology the HME 3500 (including the retaining structure 3510, if present) is sufficiently flexible that the deformation characteristics of the patient interface 3000 are not changed significantly when the HME 3500 is mounted within the plenum chamber 3200, or at least the plenum chamber is still able to be deformed. In this way the presence of the HME 3500 may not increase the likelihood of a leak path (i.e. between the seal forming structure 3100 and the patient) being created when the plenum chamber 3200 is deformed.

Referring next to FIGS. 14 to 17, in another form of the technology a patient interface may comprise a heat and moisture exchanger (HME) 3500 connected to (e.g. in contact with) the seal forming structure 3100, e.g. to the portion of the seal forming structure which is in contact with the patient's face.

In one example the patient interface 3000 may comprise a flexible heat and moisture exchange material 3502 bonded to an exterior of the seal forming structure 3100, for example as shown in FIGS. 14 and 15. The HME 3500 material may extend across the holes 3540 in the seal forming structure 3100 through which breathable gas passes to the patient's airways, such that no gas can pass from the interior of the patient interface 3000 to the patient, or from the patient to the interior of the patient interface 3000, without passing through the HME 3500.

In patient interfaces having one or more holes 3542 for gas to pass to the patient's nares and a separate hole 3544 for the patient's mouth, separate HMEs 3500 may be provided for the patient's nose and mouth, although, as shown in FIGS. 14 and 15, in examples a single HME may cover two holes 3542.

Referring next to FIG. 16, in examples the HME(s) may be connected to an interior surface of the seal forming structure 3100 rather than an exterior surface. In one example, the patient facing surface of the HME may be flush (e.g. substantially co-planar) with the patient facing surface of the seal forming structure 3100. The HME 3500 may be glued, overmoulded, or otherwise bonded to the seal forming structure 3100.

Referring next to FIG. 17, in one example the seal forming structure 3100 may comprise an engagement formation 3550 which engages an HME 3500. In the example shown the engagement formation 3550 comprises two lips 3552 which form a channel 3554 therebetween. The HME 3500 may be adhered to the channel 3554 by gluing, bonding or the like, or, in another form, no such adhesion may be required. In such examples the HME 3500 may be resiliently flexible and may be held in compression by the configuration of the engagement formation 3550. In such examples the HME 3500 may be easily removable so as to be washable and/or replaceable.

In some examples the engagement formation 3550 may be configured to hold the HME 3500 in a buckled (e.g. curved) configuration, e.g. with a concave surface facing the patient, as shown in FIG. 17.

In examples of the technology in which the HME 3500 is attached to the seal forming structure 3100, the HME 3500 may be so close to the patient's airways that the interface deadspace between the patient's airways and the HME 3500 is effectively zero, or is at least very small. In some examples, portions of the patient's face may be in contact with the HME material 3502 when the interface is in use.

In some forms of the technology a retaining structure 3510 may be provided around the perimeter of the HME 3500, but in other forms the retaining structure is not required.

As with the examples described above with reference to FIGS. 8-13, in some forms of the technology shown in FIGS. 14-17 the HME 3500 is positioned in the plenum chamber 3200 such that breathable gas entering the patient interface 3000 through the connection port 3600 can flow to the vent(s) without passing through the HME 3500.

In one form the HME material 3502 of the HMEs described above may comprise open cell reticulated polyester foam. The foam may be salted (e.g. impregnated with a salt such as calcium chloride) or unsalted. Impregnating the foam with a salt may increase its ability to absorb and desorb moisture. However, salt impregnated foam may become less effective if washed, and so non-impregnated foam may be preferred in examples in which washing of the HME 3500 is intended. In other examples a non-woven material may be used.

Referring next to FIGS. 18-23, a patient interface comprising another form of HME 3500 is shown. In the example shown in these figures the HME 3500 engages an inner surface 3202 of the plenum chamber 3200 in an interference fit.

An inner wall 3204 of the plenum chamber 3200 comprises at least one abutment formation 3206 configured to abut the HME 3500 when the HME is correctly installed within the plenum chamber 3200. The abutment formation 3206 ensures that the correct spacing is maintained between the HME 3500 and the anterior side of the patient interface and/or the vent(s) 3400. In the example shown two abutment formations 3206 are provided, one on either lateral side of the plenum chamber 3200, and the retaining structure of the HME 3500 comprises corresponding cutaway portions 3512 configured to engage posterior end portions of the abutment portions 3206. The retaining structure 3510 of the HME shown in FIGS. 18-23 does not have a shaping member, although in other examples a shaping member may be provided.

Examples of the technology may be configured for use with a variety of different types of patent interfaces, for example nasal masks, full-face masks, nasal pillows, nasal puffs and oro-nasal masks. In one example an HME 3500 as herein described may be used with a frame assembly as described in PCT application No. PCT/AU2022/050308, in particular the example shown in FIG. 17G. In examples the frame assembly may be configured to be installed within the plenum chamber 3200.

Further examples of the technology may be configured for use with the patient interface described in PCT publication No. WO2020188495, in particular the example shows in FIGS. 68-71.

4.3.10.1 Headgear Modularity

Referring next to FIGS. 24A-24C, in one example the patient interface 3000 is configured to allow the use of different types of positioning and stabilising structure, e.g. headgear. In examples the patient interface comprises a cushion module 3250 comprising the seal forming structure and, optionally, a shell 3260 which (if present) may extend between the seal forming structure and the frame. The cushion module 3250 may define, at least in part, the plenum chamber 3200. The cushion module 3250 may be configured to engage a plurality of different frames 3240 (for example by a snap fit), each frame 3240 being configured for use with a different type of headgear. FIG. 24A shows such a cushion module 3250 of such a patient interface without a frame 3240 installed. An HME 3500 is engaged within the cushion module 3250, for example in a snap fit or an interference fit.

As shown in FIG. 24B, a first frame 3240A is configured for connection to headgear comprising at least one tube 4175 that delivers pressurised air to the patient's airways and which also functions as part of the headgear to position and stabilise the seal-forming portion of the patient interface 3000 at the appropriate part of the patient's face. This type of patient interface may be referred to as having "conduit headgear" or "headgear tubing". This configuration allows the conduit in the air circuit providing the flow of pressurised air from a respiratory pressure therapy device to connect to the patient interface in a position other than in front of the patient's face. One example of such a treatment system is disclosed in US Patent Publication No. US 2007/0246043, the contents of which are incorporated herein by reference, in which the conduit connects to a tube in the patient interface through a port positioned in use on top of the patient's head.

As shown in FIG. 24C, a second frame 3240B is configured for connection to a conduit 4175 of an air circuit 4170 so that, when the patient interface is positioned on the patient's face during use, the conduit extends out of the patient interface 3000 forwards away from the patient's face. This may sometimes be referred to as a "tube down" configuration. In such examples, the conduit does not form part of the positioning and stabilising structure. Instead, a positioning and stabilising structure comprising straps (not shown) may be used, as described above. In examples a plurality of such straps may be attachable to the second frame 3240B.

A patient interface system may comprise at least the cushion module 3250, HME 3500 and both the first and second types of frame 3240A, 3240B (and optionally other types of frame and/or other components) such that a patient may decide which type of headgear to use and/or may vary the type of headgear used with the patient interface.

Each frame 3240A, 3240B may comprise at least one vent 3400, which may be provided with one or more diffusers 3402. The configuration of the vents 3400 may vary between the different frames.

4.4 RPT Device

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH2O, or at least 10 cmH2O, or at least 20 cmH2O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., filters 4110 such as an inlet air filter 4112 and outlet air filter 4114, an inlet muffler 4122, a pressure generator 4140 capable of supplying air at positive pressure (e.g., a blower 4142 comprising a motor 4144), a muffler 4120 such as an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices, a central controller, a therapy device controller, a pressure generator 4140, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

4.5 Air Circuit

An air circuit 4170 in accordance with an aspect of the present technology is a conduit or a tube constructed and arranged to allow, in use, a flow of air to travel between two components such as RPT device 4000 and the patient interface 3000 or 3800.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

4.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000 or 3800.

4.6 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

In examples the humidifier reservoir further comprises a conductive portion 5120, a locking lever 5135 and a water level indicator 5150.

In one form of the present technology, an anti-spill back valve 4160 is located between the humidifier 5000 and the pneumatic block 4020.

In some forms of the technology an RPT for use with a patient interface of the present technology may not require a humidifier.

4.7 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

4.8 Glossary

For the purposes of the present technology disclosure, in certain forms of the present technology, one or more of the following definitions may apply. In other forms of the present technology, alternative definitions may apply.

4.8.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal (1 hectopascal=100 Pa=100 N/$m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

4.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

4.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH2O pressure.

As an example, an I-beam may comprise a different bending stiffness (resistance to a bending load) in a first direction in comparison to a second, orthogonal direction. In another example, a structure or component may be floppy in a first direction and rigid in a second direction.

4.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peakflow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

Inhalation Time (Ti): The duration of the inspiratory portion of the respiratory flow rate waveform.

Exhalation Time (Te): The duration of the expiratory portion of the respiratory flow rate waveform.

Total Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.8.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\pi(\Phi)$ is zero-valued at the end of expiration, i.e. $\pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts, pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator, or other respiratory therapy device such as an RPT device or portable oxygen concentrator, delivers a volume of breathable gas to a spontaneously breathing patient, it is said to be triggered to do so. Triggering usually takes place at or near the initiation of the respiratory portion of the breathing cycle by the patient's efforts.

4.8.4 Anatomy 4.8.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

*Glabella*: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture. Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 4.8.4.2 Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.8.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.8.5 Patient Interface

Anti-asphyxia valve (AAV): The component or sub-assembly of a mask system that, by opening to atmosphere in a failsafe manner, reduces the risk of excessive CO2 rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

4.8.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

4.8.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

4.8.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

4.8.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

4.8.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections there-through in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

4.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

4.10 REFERENCE SIGNS LIST

| | |
|---|---|
| patient | 1000 |
| bed partner | 1100 |
| patient interface | 3000 |
| seal forming structure | 3100 |
| plenum chamber | 3200 |
| inner surface | 3202 |
| inner wall | 3204 |
| abutment formation | 3206 |
| chord | 3210 |
| superior point | 3220 |
| inferior point | 3230 |

-continued

| 4.10 REFERENCE SIGNS LIST | |
|---|---|
| frame | 3240 |
| first frame | 3240A |
| second frame | 3240B |
| cushion module | 3250 |
| shell | 3260 |
| positioning and stabilising structure | 3300 |
| vent | 3400 |
| diffuser | 3402 |
| HME | 3500 |
| HME material | 3502 |
| retaining structure | 3510 |
| cutaway | 3512 |
| snap fit feature | 3520 |
| snap fit feature | 3522 |
| channel | 3524 |
| rib | 3526 |
| first face | 3530 |
| second face | 3532 |
| shaping member | 3534 |
| interface deadspace | 3536 |
| openings | 3540 |
| hole for nose | 3542 |
| hole for mouth | 3544 |
| engagement formation | 3550 |
| lips | 3552 |
| channel | 3554 |
| connection port | 3600 |
| forehead support | 3700 |
| patient interface | 3800 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| air filter | 4110 |
| inlet air filter | 4112 |
| muffler | 4120 |
| outlet muffler | 4124 |
| pressure generator | 4140 |
| blower | 4142 |
| motor | 4144 |
| anti-spillback valve | 4160 |
| air circuit | 4170 |
| tube | 4175 |
| supplementary gas | 4180 |
| electrical components | 4200 |
| PCBA | 4202 |
| electrical power supply | 4210 |
| input device | 4220 |
| transducers | 4270 |
| humidifier | 5000 |
| humidifier inlet | 5002 |
| humidifier outlet | 5004 |
| humidifier base | 5006 |
| humidifier reservoir | 5110 |
| conductive portion | 5120 |
| reservoir dock | 5130 |
| locking lever | 5135 |
| water level indicator | 5150 |
| heating element | 5240 |

The invention claimed is:

1. A patient interface comprising:

a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

a positioning and stabilising structure to provide a force to hold the seal-forming structure in a therapeutically effective position on the patient's head, and a vent structure to allow a continuous flow of gases exhaled by the patient from an interior of the plenum chamber to ambient, said vent structure being sized and shaped to maintain the therapeutic pressure in the plenum chamber in use;

wherein the patient interface is configured to allow the patient to breath from ambient through their mouth in the absence of a flow of pressurised air through the plenum chamber inlet port, or the patient interface is configured to leave the patient's mouth uncovered; and wherein patient interface comprises a flexible heat and moisture exchanger (HME) located within the plenum chamber, the HME comprising a flexible heat and moisture exchange material and a retaining structure formed from a pliable material provided around an outer perimeter of the heat and moisture exchange material, wherein: the interior of the plenum chamber comprises at least one snap fit feature, and the retaining structure comprises at least one complementary snap fit feature comprising a rib, the at least one complementary snap fit feature being configured to engage, in use, the at least one snap fit feature located on the interior of the plenum chamber.

2. The patient interface of claim 1, wherein the heat and moisture exchange material comprises a foam.

3. The patient interface of claim 1, wherein the heat and moisture exchange material comprises a non-woven material.

4. The patient interface of claim 1, wherein the retaining structure is formed from a flexible thermoplastic.

5. The patient interface of claim 4, wherein the retaining structure is formed by overmoulding.

6. The patient interface of claim 1, wherein the plenum chamber is formed, at least in part, from a flexible material.

7. The patient interface of claim 1, wherein the heat and moisture exchange material has a patient facing side and a non patient facing side, and wherein the patient facing side of the heat and moisture exchange material is concave.

8. The patient interface of claim 7, wherein the retaining structure comprises a shaping member which extends across the patient facing side of the heat and moisture exchange material, wherein the shaping member is configured to impart the concave shape to the patient facing side of the heat and moisture exchange material.

9. The patient interface of claim 1, wherein the patient interface is configured to allow air to flow from the inlet port to the vent structure without passing through the HME.

10. The patient interface of claim 1, wherein the retaining structure comprises a snap fit feature which comprises a channel which extends at least partially around the outer perimeter of the retaining structure.

11. The patient interface of claim 10, wherein the channel extends around the entire outer perimeter of the retaining structure.

12. The patient interface of claim 1, wherein the rib extends at least partially around the outer perimeter of the retaining structure.

13. The patient interface of claim 1, wherein the HME is configured to provide at least 10 mg/L humidification.

14. A patient interface comprising:

a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

a positioning and stabilising structure to provide a force to hold the seal-forming structure in a therapeutically effective position on the patient's head, and a vent structure to allow a continuous flow of gases exhaled by the patient from an interior of the plenum chamber to ambient, said vent structure being sized and shaped to maintain the therapeutic pressure in the plenum chamber in use;

wherein the patient interface is configured to allow the patient to breath from ambient through their mouth in the absence of a flow of pressurised air through the plenum chamber inlet port, or the patient interface is configured to leave the patient's mouth uncovered; and wherein patient interface comprises a flexible heat and moisture exchanger (HME) located within the plenum chamber, the HME comprising a flexible heat and moisture exchange material and a retaining structure formed from a pliable material provided around an outer perimeter of the heat and moisture exchange material, wherein the interior of the plenum comprises a rib; wherein the channel is configured to engage the rib of the interior of the plenum chamber in a snap fit.

15. The patient interface of claim 14, wherein the patient interface is configured to allow air to flow from the inlet port to the vent structure without passing through the HME.

* * * * *